(12) United States Patent
Chee

(10) Patent No.: US 6,607,887 B2
(45) Date of Patent: *Aug. 19, 2003

(54) COMPUTER-AIDED VISUALIZATION AND ANALYSIS SYSTEM FOR SEQUENCE EVALUATION

(75) Inventor: Mark S. Chee, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/796,071

(22) Filed: Feb. 27, 2001

(65) Prior Publication Data

US 2002/0012925 A1 Jan. 31, 2002

Related U.S. Application Data

(63) Continuation of application No. 09/158,765, filed on Sep. 23, 1998, now Pat. No. 6,242,180, which is a continuation of application No. 08/531,137, filed on Oct. 16, 1995, now Pat. No. 5,974,164, which is a continuation-in-part of application No. 08/327,525, filed on Oct. 21, 1994, now Pat. No. 5,795,716.

(51) Int. Cl.⁷ .......................... C12Q 1/68; C07H 21/04; G01N 31/00
(52) U.S. Cl. .............................. 435/6; 536/23.1; 702/27
(58) Field of Search .............................. 435/6; 536/23.1; 702/27

(56) References Cited

U.S. PATENT DOCUMENTS

| | | | |
|---|---|---|---|
| 4,720,786 A | 1/1988 | Hara | 364/413 |
| 4,741,043 A | 4/1988 | Bacus | 382/6 |
| 4,777,597 A | 10/1988 | Shiraishi et al. | 364/413.01 |
| 4,802,101 A | 1/1989 | Hara | 364/496 |
| 4,811,218 A | 3/1989 | Hunkapiller et al. | 364/413.13 |
| 4,837,733 A | 6/1989 | Shiraishi et al. | 364/413.13 |
| 4,885,696 A | 12/1989 | Hara | 364/497 |
| 4,888,695 A | 12/1989 | Shiraishi et al. | 364/413.13 |
| 4,894,786 A | 1/1990 | Hara | 364/497 |
| 4,939,667 A | 7/1990 | Hara et al. | 364/497 |
| 4,941,092 A | 7/1990 | Hara et al. | 364/431.15 |
| 4,958,281 A | 9/1990 | Hara | 364/413.01 |
| 4,965,725 A | 10/1990 | Rutenberg | 364/413.1 |
| 4,972,325 A | 11/1990 | Hara | 364/497 |
| 4,980,827 A | 12/1990 | Hara | 382/129 |
| 4,982,326 A | 1/1991 | Kaneko | 364/413.01 |
| 5,002,867 A | 3/1991 | Macevicz | 435/6 |
| 5,143,854 A | 9/1992 | Pirrung et al. | 436/518 |
| 5,202,231 A | 4/1993 | Drmanac et al. | 435/6 |
| 5,235,626 A | 8/1993 | Flamholz et al. | 378/34 |
| 5,260,190 A | 11/1993 | Shiraishi et al. | 435/6 |
| 5,270,162 A | 12/1993 | Shiraishi et al. | 435/6 |
| 5,273,632 A | 12/1993 | Stockham et al. | 204/180.1 |
| 5,288,514 A | 2/1994 | Ellman | 427/2 |
| 5,297,288 A | 3/1994 | Hemminger et al. | 395/700 |
| 5,306,618 A | 4/1994 | Prober et al. | 435/6 |
| 5,332,666 A | 7/1994 | Prober et al. | 435/91 |
| 5,384,261 A | 1/1995 | Winkler et al. | 436/518 |
| 5,445,934 A | 8/1995 | Fodor et al. | 435/6 |
| 5,470,710 A | 11/1995 | Weiss et al. | 435/6 |
| 5,492,806 A | 2/1996 | Drmanac | 435/5 |
| 5,525,464 A | 6/1996 | Drmanac et al. | 435/6 |
| 5,527,681 A | 6/1996 | Holmes | 435/6 |
| 5,556,749 A | 9/1996 | Mitsuhashi et al. | 435/6 |
| 5,665,549 A | 9/1997 | Pinkel et al. | 435/6 |
| 5,727,098 A | 3/1998 | Jacobson | 385/31 |
| 6,242,180 B1 * | 6/2001 | Chee | 435/6 |

FOREIGN PATENT DOCUMENTS

| | | |
|---|---|---|
| EP | 0514927 A1 | 5/1992 |
| EP | 0549388 A1 | 6/1993 |
| EP | 0631635 | 9/1993 |
| EP | 0677194 | 5/1994 |
| FR | 2684688 | 6/1993 |
| WO | WO 89/10977 | 11/1989 |

(List continued on next page.)

OTHER PUBLICATIONS

Fodor et al., "Light–Directed, Spatially Addressable Parallel Chemical Synthesis," Science, vol. 251, Feb. 15, 1991, pp. 767–773.

Brown et al., An Inexpensive MSI/LSI Mask Making System, Proceedings of 1981 Univ. Govt. Indus. Microelec. Symposium, May 26–27, 1981, pp. III–31 through III–38.

Dear et al., "A Sequence Assembly And Editing Program For Efficient Management of Large Projects," Nucleic Acids Research, vol. 19, No. 14, 1991 Oxford Univ. Press, pp. 3907–3911.

Drmanac et al. "An Algorithm for the DNA Sequence Generation Form k–Tuple Word Contents of the Minimal Number of Random Fragments", 1991; J. of Biomolecular Structure & Dynamics 8: 1085–1102.

Drmanac et al. DNA Sequence Determination by Hybridization: A Strategy for Efficient Large Scale Sequencing. 1993; Science: 260:1649–1652.

Strezoska et al. DNA Sequencing by Hybridization: 100 Bases Read by a Non–Gel Based Method. 1991. PNAS 88: 10089–10093.

Southern et al. Analyzing and Comparing Nucleic Acid Sequences by Hybridization to Arrays of Oligonucleotides: Evaluation Using Experimental Models. 1992. Genomics 13: 1008–1017.

*Primary Examiner*—Kenneth R. Horlick
*Assistant Examiner*—Young Kim
(74) *Attorney, Agent, or Firm*—Ritter, Lang & Kaplan LLP

(57) ABSTRACT

A computer system for analyzing nucleic acid sequences is provided. The computer system is used to perform multiple methods for determining unknown bases by analyzing the fluorescence intensities of hybridized nucleic acid probes. The results of individual experiments may be improved by processing nucleic acid sequences together. Comparative analysis of multiple experiments is also provided by displaying reference sequences in one area and sample sequences in another area on a display device.

13 Claims, 31 Drawing Sheets

Microfiche Appendix Included
(5 Microfiche, 272 Pages)

FOREIGN PATENT DOCUMENTS

| | | |
|---|---|---|
| WO | WO 90/01564 | 2/1990 |
| WO | WO 92/10092 | 6/1992 |
| WO | WO 92/10588 | 6/1992 |
| WO | WO 92/20824 | 11/1992 |
| WO | WO 93/11262 | 6/1993 |
| WO | WO 93/18186 | 9/1993 |
| WO | WO 94/11837 | 5/1994 |
| WO | WO 95/11995 | 5/1995 |
| WO | WO/ 95/35505 | 12/1995 |

* cited by examiner

REFERENCE SEQUENCE  A C T₁ G₂ T₃ T₄ A₅ G C T A A T T G G - 5'

| | | | | | |
|---|---|---|---|---|---|
| WT-LANE | T G A C | G A C A | A C A A | C A A T | A A T G |
| A-LANE  | T G A C | G A A A | A C A A | C A A T | A A A G |
| C-LANE  | T G C C | G A C A | A C C A | C A C T | A A C G |
| G-LANE  | T G G C | G A G A | A C G A | C A G T | A A G G |
| T-LANE  | T G T C | G A T A | A C T A | C A T T | A A T G |
| | I₁ | I₂ | I₃ | I₄ | I₅ |

REFERENCE SEQUENCE  A C T G T T A G C T A A T T G G

WT-LANE
A-LANE
C-LANE
G-LANE
T-LANE

I₁ I₂ I₃ I₄ I₅

| POSITION | WT | REFERENCE | | | | SAMPLE | | | | | RATIO OF RATIOS | | | | BASE | CONFIDENCE |
|---|---|---|---|---|---|---|---|---|---|---|---|---|---|---|---|---|
| | | BACK-GROUND | A | C | G | T | BACK-GROUND | A | C | G | T | A/A | C/C | G/G | T/T | | |
| 463 | C | P | 7.2 | 9.9 | 1.0 | 5.6 | P | 6.4 | 2.3 | 1.0 | 14.5 | 1.1 | 4.3 | 1.0 | 0.4 | G | 1 |
| 1 | 2 | 3 | 4 | 5 | 6 | 7 | 8 | 9 | 10 | 11 | 12 | 13 | 14 | 15 | 16 | 17 | 18 |

FIG. 10B

| BCK SUBTRACTED INTENSITIES | | | | | | | | | | | | | | | | | | |
|---|---|---|---|---|---|---|---|---|---|---|---|---|---|---|---|---|---|---|
| RY090203.CQ1 | -7 | -6 | -5 | -4 | -3 | -2 | -1 | 0 | 1 | 2 | 3 | 4 | 5 | 6 | 7 | 8 | 9 | |
| POSITION: | 234 | 235 | 236 | 237 | 238 | 239 | 240 | 241 | 242 | 243 | 244 | 245 | 246 | 247 | 248 | 249 | 250 | |
| WILDTYPE: | A | A | A | C | C | C | A | A | T | C | C | A | C | A | T | C | A | |
| CALLED: | A | A | A | C | C | C | A | A | T | C | C | A | C | A | T | C | M | 502A |
| A | 148 | 193 | 165 | 17 | 70 | 38 | 282 | 385 | 97 | 31 | 18 | 158 | 15 | 223 | 178 | 126 | 154 | |
| C | 57 | 100 | 42 | 167 | 345 | 278 | 38 | 99 | 139 | 249 | 249 | 13 | 244 | 28 | 257 | 250 | 175 | |
| G | 26 | 32 | 20 | 16 | 64 | 17 | 27 | 107 | 100 | 13 | 9 | 11 | 10 | 30 | 142 | 59 | 55 | |
| T | 9 | 15 | 10 | 6 | 41 | 14 | 27 | 79 | 261 | 6 | 2 | 1 | 7 | 16 | 320 | 52 | 37 | |
| S | 240 | 340 | 238 | 207 | 522 | 347 | 374 | 671 | 598 | 298 | 279 | 182 | 276 | 298 | 896 | 487 | 421 | |
| WTR | 148 | 193 | 165 | 167 | 345 | 278 | 282 | 385 | 261 | 249 | 249 | 158 | 244 | 223 | 320 | 250 | 154 | |
| MAXR | 148 | 193 | 165 | 167 | 345 | 278 | 282 | 385 | 261 | 249 | 249 | 158 | 244 | 223 | 320 | 250 | 175 | |
| MC090407.CQ1 | | | | | | | | | | | | | | | | | | |
| POSITION: | 234 | 235 | 236 | 237 | 238 | 239 | 240 | 241 | 242 | 243 | 244 | 245 | 246 | 247 | 248 | 249 | 250 | |
| WILDTYPE: | A | A | A | C | C | C | A | A | T | C | C | A | C | A | T | C | A | |
| CALLED: | M | M | A | C | X | C | A | X | X | C | C | A | C | A | X | X | M | 502B |
| A | 194 | 238 | 150 | 44 | 191 | 126 | 283 | 332 | 234 | 58 | 49 | 242 | 25 | 337 | 286 | 180 | 256 | |
| C | 209 | 291 | 74 | 202 | 337 | 277 | 74 | 199 | 175 | 259 | 288 | 27 | 376 | 65 | 379 | 324 | 234 | |
| G | 92 | 72 | 34 | 29 | 114 | 52 | 65 | 571 | 231 | 30 | 17 | 16 | 47 | 71 | 254 | 104 | 109 | |
| T | 25 | 39 | 16 | 11 | 96 | 29 | 68 | 205 | 267 | 11 | 8 | 5 | 23 | 57 | 427 | 97 | 85 | |
| S | 520 | 639 | 274 | 286 | 738 | 484 | 489 | 1307 | 906 | 357 | 362 | 291 | 472 | 529 | 1346 | 705 | 684 | |
| WTR | 194 | 238 | 150 | 202 | 337 | 277 | 283 | 332 | 267 | 259 | 288 | 242 | 376 | 337 | 427 | 324 | 256 | |
| MAXR | 209 | 291 | 150 | 202 | 337 | 277 | 283 | 571 | 267 | 259 | 288 | 242 | 376 | 337 | 427 | 324 | 256 | |

*FIG. 11B*

| | | | | | | | | | | | | | | | | 530 | 532 |
|---|---|---|---|---|---|---|---|---|---|---|---|---|---|---|---|---|---|
| WTE/WTR | 1.31 | 1.23 | 0.91 | 1.21 | 0.98 | 1.00 | 1.00 | 0.86 | 1.02 | 1.04 | 1.15 | 1.54 | 1.54 | 1.51 | 1.34 | 1.30 | 1.66 |
| MAXE/WTR | 1.42 | 1.51 | 0.91 | 1.21 | 0.98 | 1.00 | 1.00 | 1.48 | 1.02 | 1.04 | 1.15 | 1.54 | 1.54 | 1.51 | 1.34 | 1.30 | 1.66 |
| N-L + N-R | | 0.79 | -0.63 | 0.54 | -0.25 | 0.01 | 0.14 | 0.94 | 0.14 | -0.10 | -0.27 | 0.38 | 0.04 | 0.14 | -0.13 | -0.40 | |
| N-L | | 0.09 | -0.60 | 0.30 | -0.24 | 0.02 | 0.01 | 0.48 | -0.46 | 0.02 | 0.11 | 0.38 | 0.01 | -0.04 | -0.17 | -0.04 | |
| N-R | | 0.60 | -0.30 | 0.24 | -0.02 | -0.01 | -0.48 | 0.46 | -0.02 | -0.11 | -0.38 | -0.01 | 0.04 | 0.17 | 0.04 | -0.36 | |
| N-L D(N-R) | | | -0.90 | 0.54 | -0.25 | 0.01 | -0.48 | 0.94 | -0.48 | -0.10 | -0.27 | 0.38 | 0.04 | 0.14 | 0.04 | | |
| N-R D(N-L) | | | -0.90 | 0.54 | -0.25 | 0.01 | -0.48 | 0.94 | -0.48 | -0.10 | -0.27 | 0.38 | 0.04 | 0.14 | -0.13 | | |
| L(N-L) - (N-R)L | | | 0.29 | 0.07 | 0.22 | 0.02 | 0.49 | 0.02 | 0.44 | 0.13 | 0.50 | 0.39 | 0.03 | 0.06 | 0.21 | | |
| A+B-C | | | -2.10 | 1.01 | -0.73 | 0.00 | -1.44 | 1.86 | -1.40 | -0.33 | -1.03 | 0.36 | 0.06 | 0.06 | -0.48 | | |
| SUM MT/ SUM WT | | | | | | | | | | | | | | | | | |
| INTENSITIES | | | | | | | | | | | | | | | | | |
| N/L + N/R | 2.16 | 1.88 | 1.15 | 1.39 | 1.41 | 1.39 | 1.31 | 1.95 | 1.52 | 1.20 | 1.30 | 1.60 | 1.71 | 1.78 | 1.50 | 1.45 | 1.63 |
| N-L + N-R | | 2.50 | 1.45 | 2.18 | 2.04 | 2.05 | 1.61 | 2.77 | 2.04 | 1.71 | 1.89 | 2.18 | 2.03 | 2.22 | 1.88 | 1.85 | |
| N-L | | 0.22 | -0.48 | 0.10 | 0.02 | 0.03 | -0.36 | 0.54 | -0.06 | -0.21 | -0.10 | 0.10 | 0.02 | 0.17 | -0.11 | -0.12 | |
| N-R | | -0.28 | -0.73 | 0.21 | 0.03 | -0.02 | -0.09 | 0.54 | -0.43 | -0.32 | 0.10 | 0.30 | 0.10 | 0.07 | -0.27 | -0.06 | |
| | | 0.73 | -0.23 | -0.03 | 0.02 | 0.09 | -0.64 | 0.43 | 0.32 | -0.10 | -0.30 | -0.10 | -0.07 | 0.27 | 0.06 | -0.18 | |

| | | | | | | | | | | 510 | | | | | | 518 | | | | | 524 | |
|---|---|---|---|---|---|---|---|---|---|---|---|---|---|---|---|---|---|---|---|---|---|---|
| NORMALIZED INTENSITIES | | | | | | | | | | | | | | | | | | | | | | |
| WILDTYPE | | | | | | | | | | | | | | | | | | | | | | |
| A | 0.61 | 0.57 | 0.70 | 0.08 | 0.13 | 0.11 | 0.75 | 0.57 | 0.16 | 0.10 | 0.07 | 0.87 | 0.06 | 0.75 | 0.20 | 0.26 | 0.37 |
| C | 0.24 | 0.29 | 0.18 | 0.81 | 0.66 | 0.80 | 0.10 | 0.15 | 0.23 | 0.83 | 0.90 | 0.07 | 0.88 | 0.09 | 0.29 | 0.51 | 0.42 |
| G | 0.11 | 0.09 | 0.08 | 0.08 | 0.12 | 0.05 | 0.07 | 0.16 | 0.17 | 0.04 | 0.03 | 0.06 | 0.04 | 0.10 | 0.16 | 0.12 | 0.13 |
| T | 0.04 | 0.04 | 0.04 | 0.03 | 0.08 | 0.04 | 0.07 | 0.12 | 0.44 | 0.02 | 0.01 | 0.01 | 0.03 | 0.05 | 0.36 | 0.11 | 0.09 |
| MUTANT | | | | | | | | | | | | | | | | | | | | | | |
| A | | 0.37 | 0.55 | 0.15 | 0.26 | 0.26 | 0.58 | 0.25 | 0.26 | 0.16 | 0.16 | 0.83 | 0.05 | 0.64 | 0.21 | 0.26 | 0.37 |
| C | 0.40 | 0.45 | 0.27 | 0.71 | 0.46 | 0.57 | 0.15 | 0.15 | 0.19 | 0.72 | 0.80 | 0.09 | 0.80 | 0.12 | 0.28 | 0.46 | 0.34 |
| G | 0.18 | 0.11 | 0.12 | 0.10 | 0.15 | 0.11 | 0.13 | 0.44 | 0.16 | 0.08 | 0.05 | 0.06 | 0.10 | 0.13 | 0.19 | 0.15 | 0.16 |
| T | 0.05 | 0.06 | 0.06 | 0.04 | 0.13 | 0.06 | 0.14 | 0.16 | 0.29 | 0.03 | 0.02 | 0.02 | 0.05 | 0.11 | 0.32 | 0.14 | 0.12 |
| MT - MT (NORMALIZED INTENSITIES) | | | | | | | | | | | | | | | | | | | | | | |
| POSITION: | 234 | 235 | 236 | 237 | 238 | 239 | 240 | 241 | 242 | 243 | 244 | 245 | 246 | 247 | 248 | 249 | 250 |
| WILDTYPE: | A | A | A | C | C | C | A | A | T | C | C | A | C | A | T | C | A |
| CALLED: | M | M | A | C | X | C | A | X | X | C | C | A | C | A | X | X | M |
| A | -0.24 | -0.20 | -0.15 | 0.07 | 0.12 | 0.15 | -0.18 | -0.32 | 0.09 | 0.06 | 0.07 | -0.04 | 0.00 | -0.11 | 0.01 | 0.00 | 0.01 |
| C | 0.17 | 0.16 | 0.09 | -0.10 | -0.20 | -0.23 | 0.05 | 0.00 | -0.04 | -0.11 | -0.10 | 0.03 | -0.08 | 0.03 | -0.01 | -0.05 | -0.07 |
| G | 0.07 | 0.02 | 0.04 | 0.02 | 0.03 | 0.06 | 0.06 | 0.28 | 0.09 | 0.04 | 0.01 | 0.00 | 0.06 | 0.03 | 0.03 | 0.03 | 0.03 |
| T | 0.01 | 0.02 | 0.02 | 0.01 | 0.05 | 0.02 | 0.07 | 0.04 | -0.14 | 0.01 | 0.01 | 0.01 | 0.02 | 0.05 | -0.04 | 0.03 | 0.04 |

FIG. 19

```
tcgagataatctatgtcctgtcatatgtcatatcttcttacttaaacggtcctttacctttggttttactatc  CONSENSUS
         90        100       110       120       130       140       150       160
nngagatannnntatgtcctcgtcgtcgtcgtcgtcgtcgtcgtcgtcyactatgtnannnnnnnnnnnnnnnaaacggtcctnnnnnnnnnnnnnnnnnnnnwn
tcgagataatctatgtcctcgtcgtcgtcgtcgtcgtcgtcgtcgtcgtcgtcgtcgtcyactatgtcatatgtcatatnnnnnnnnnnnnnactnaaacggtcctttacctttggttttactatc   PRE-TREATMENT
tcgagataatctatgtcctcgtcgtcgtcgtcgtcgtcgtcgtcyactatgtcatatgtcatatcttcttacttaaacggtcctttacctttggttttactatc
tcgagataatctatgtcctcgtcgtcgtcgtcgtcgtcgtcgtcyactatgtcatatgtcatatcttcttacttaaacggtcctttacctttggttttactatc
tcgagataatctatgtcctcgtcgtcgtcgtcgtcgtcgtcgtcyactatgtcatatgtcatatcttcttacttaaacggtcctttacctttggttttactatc
ncgggataantntatgtcctcgtcgtcgtcgtcgtcgtcgtcyactatgtcannnnncnnncnnncaaaacggtcchccnnnnncnnnnncnnncyaha
tcgrgataatctatgtcctcgtcgtcgtcgtcgtcgtcgtcgtccgtcgtcgtcatatccnnncnnctcaaaacggtcctyccnnnnytggttnytactatc   POST-TREATMENT
tcgagataatctatgtcctcgtcgtcgtcgtcgtcgtcgtcgtcgtcgtcgtcatatcchnnctactcaaaacggtcctnctacctttggttttactatc
tcgagataatctatgtcctcgtcgtcgtcgtcgtcgtcgtcgtcgtcgtcatatcttcttacycaaaacggtcctxctacctttggttttactatc cccttaacctccaaaatagtttcattctgtcatgctagtctagtctatggacatctttagacacctgtatttcgatatccatgt  CONSENSUS
         170       180       190       200       210       220       230       240
cnncntaacctccaaaatannnnnnnntctnnnnnannnntctannngnagnnnnagananrnccnnnnnnnnnnatncatgt
cccttaacctccaaaatagtttcattctgtcattctgncatannagtctatgngngngnnnntagacagncnmnnntcgatatccatgt   PRE-TREATMENT
cmmcttaacctccaaaatagtttcattctgtcattctgtcatactagtctagtctatggtagcttagacamccgtatttcgatatccatgt
cccttaacctccaaaatagtttcattctgtcattctgtcatactagtctagtctatggtagcttagacacccgtatttcgatatccatgt
ccmcttaacctccaaaatannnnnnnntctnnnnnaannncnctnnnnnnagngnnagacacctgtatnnnnntatncaygt
aawcycaacctccaaaatagtttcattctgtcattctgncatacnnstctannxnnagxgttagacacctgtatttcgatatccatgt   POST-TREATMENT
cccttaacctccaaaatagtttcattctgtcattctgtcatactagtctatgagtagcttagacacctgtatttcgatatccatgt
cmcctaacctccaaaatagtttcattctgtcattctgtcatactagtctatgagtagcttagacacctgtatttcgatatccatgt
ccmcttaacctccaaaatagtttcattctgtcattctgtcatactagtctatgagtagcttagacacctgtatttcgatatccatgt
```

FIG. 21

```
                        SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 1:

ATGTGGACAG TTGTA                                                    15

(2) INFORMATION FOR SEQ ID NO: 2:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 2:

ATGTGGATAG TTGTA                                                    15

(2) INFORMATION FOR SEQ ID NO: 3:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 3:

ATGTGGAKAG TTGTA                                                    15

(2) INFORMATION FOR SEQ ID NO: 4:

(i) SEQUENCE CHARACTERISTICS:
         (A) LENGTH: 11 base pairs
         (B) TYPE: nucleic acid
         (C) STRANDEDNESS: single
```

(D) TOPOLOGY: linear (ii) MOLECULE TYPE: DNA (oligonucleotide)

(xi) SEQUENCE DESCRIPTION: SEQ ID NO: 4:

AAAACTGAAA A                                                                11

(2) INFORMATION FOR SEQ ID NO: 5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 5:

AAAACCGAAA A                                                                11

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 6:

AAACCCAATC CACATCA                                                          17

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 7:

AAACCCAGTC CACATCA                                                          17

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 8:

GGGGAAGCAG ATTTGGGTAC CACCCAAGTA T                                          31

(2) INFORMATION FOR SEQ ID NO: 9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 9:

GGGGAAGCAG ATTTGAAMAC CACCCAAGTA T                               31

(2) INFORMATION FOR SEQ ID NO: 10:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 10:

GCATTAGTAG AGATATGTAC AGAAATGGAA AAGGAAGGGA AAATTTCAAA AATTGGGCC      59

(2) INFORMATION FOR SEQ ID NO: 11:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 11:

GCATTAGTAG AAATTTGTAC AGAGATGGAA AAGGAAGGGA AAATTTCAAA AATTGGGCC      59

(2) INFORMATION FOR SEQ ID NO: 12:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 12:

GCATTAGTAG AGATATGGAG AGRARDGGRA ANNNAAGGGA AAATTNNNAA AATTGGGCC      59

(2) INFORMATION FOR SEQ ID NO: 13:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 13:

GCATTAGTAG AGATATGKAS AGRARDGGRA ANNNAAGGGA AAAKTNNNAA AATTGGGCC      59

(2) INFORMATION FOR SEQ ID NO: 14:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 14:

GCATTAGTAG AGATATGKAS AGRRRDGGRA ANNNAAGGGA AAADTYNNAA AATTGGGCC      59

(2) INFORMATION FOR SEQ ID NO: 15:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 15:

```
GCATTAGTAG AGATATGTAS AGRRADGGAA ANGGAAGGGA AAATTNNNNA AATTGGGCC    59
```

(2) INFORMATION FOR SEQ ID NO: 16:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 16:

```
GCATTAGTAG AGATATGTAC AGRGAGGGAA ANGGAAGGGA AAATTNNNNA AATTGGGCC    59
```

(2) INFORMATION FOR SEQ ID NO: 17:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 17:

```
GCATTAGTAG AGATATGTAS AGRGAGGGAA ANGGAAGGGA AAATTNNNNA AATTGGGCC    59
```

(2) INFORMATION FOR SEQ ID NO: 18:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 18:

```
GCATTAGTAG GAGGNNNGAC AGGGRKGGAA ANNMAAGGGA AAAKTNNNAA AATTGGGCC    59
```

(2) INFORMATION FOR SEQ ID NO: 19:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 19:

```
TCGAGATAAT CTATGTCCTC GTCTACTATG TCATAATCTT CTTTACTTAA ACGGTCCTTT    60
TACCTTTGGT TTTTACTATC CCCCTTAACC TCCAAAATAG TTTCATTCTG TCATGCTAGT   120
CTATGGACAT CTTTAGACAC CTGTATTTCG ATATCCATGT                         160
```

(2) INFORMATION FOR SEQ ID NO: 20:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 20:

```
NNGAGATANN NTATGTCCTC GTCYACTATG TNANNNNNNN NNNNNNNNAA ACGGTCCTNN   60
NNNNNNNNNN NNNNNNNNNN CNNCNTAACC TCCAAAATAN NNNNNNTCTN NNNNANNNNT  120
CTANNNGNAG NNNNAGANAR NCCNNNNNNN NNATNCATGT                        160
```

(2) INFORMATION FOR SEQ ID NO: 21:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 21:

```
TCGAGATAAT CTATGTCCTC GTCTACTATG TCATAATNNN NNNNACTTAA ACGGTCCTTT   60
TACCTTTGGT TTTTACTATC CCCCTTAACC TCCAAAATAG TTTCATTCTG NCATANNAGT  120
CTATGNGNNG NNNTAGACAG NCCNNNNTCG ATATCCATGT                        160
```

(2) INFORMATION FOR SEQ ID NO: 22:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 22:

```
TCGAGATAAT CTATGTCCTC GTCTACTATG TCATAATCTT CTTTACTTAA ACGGTCCTTT   60
TACCTTTGGT TTTTACTATC CNNCTTAACC TCCAAAATAG TTTCATTCTG TCATACTAGT  120
CTATGGGTAG CTTTAGACCN CCGTATTTCG ATATCCATGT                        160
```

(2) INFORMATION FOR SEQ ID NO: 23:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 23:

```
TCGAGATAAT CTATGTCCTC GTCTACTATG TCATAATCTT CTTTACTTAA ACGGTCCTTT   60
TACCTTTGGT TTTTACTATC CCNCTTAACC TCCAAAATAG TTTCATTCTG TCATACTAGT  120
CTATGGGTAG CTTTAGACCC CCGTATTTCG ATATCCATGT                        160
```

(2) INFORMATION FOR SEQ ID NO: 24:

(i) SEQUENCE CHARACTERISTICS:
            (A) LENGTH: 160 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 24:

NCGGGATANT NTATGTCCTC GTCYACTATG TCANNNNNCN NNCNNNNCAA ACGGTCCNCC   60

NNNNNCNNNN NNCNNCYANG AANCYCAACC TCCAAAATAN NNNNNNTCTN NNNNANNNCN  120

CTNNNNNNAG NGNNAGACAC CTGTATNNNN NTATNCAYGT                       160

(2) INFORMATION FOR SEQ ID NO: 25:

(i) SEQUENCE CHARACTERISTICS:
            (A) LENGTH: 160 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 25:

TCGRGATAAT CTATGTCCTC GTCTACTATG TCATAATCCN NNCNNCTCAA ACGGTCCTYC   60

CNNNNYTGGT TNYTACTATC CCCCTTAACC TCCAAAATAG TTTCATTCTG NCATACNNST  120

CTANNNNNAG NGTTAGACAC CTGTATTTCG ATATCCATGT                       160

(2) INFORMATION FOR SEQ ID NO: 26:

(i) SEQUENCE CHARACTERISTICS:
            (A) LENGTH: 160 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 26:

TCGAGATAAT CTATGTCCTC GTCTACTATG TCATAATCCN NCCTACTCAA ACGGTCCTTC   60

TACCTTTGGT TTTTACTATC CMCCTTAACC TCCAAAATAG TTTCATTCTG TCATACTAGT  120

CTATGAGTAG CTTTAGACAC CTGTATTTCG ATATCCATGT                       160

(2) INFORMATION FOR SEQ ID NO: 27:

(i) SEQUENCE CHARACTERISTICS:
            (A) LENGTH: 160 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 27:

TCGAGATAAT CTATGTCCTC GTCTACTATG TCATAATCTT CTTTACYCAA ACGGTCCTXC   60

TACCTTTGGT TTTTACTATC CCMCTTAACC TCCAAAATAG TTTCATTCTG TCATACTAGT  120

CTATGAGTAG CTTTAGACAC CTGTATTTCG ATATCCATGT                       160

(2) INFORMATION FOR SEQ ID NO: 28:

(i) SEQUENCE CHARACTERISTICS:
            (A) LENGTH: 17 base pairs
            (B) TYPE: nucleic acid (C) STRANDEDNESS: single
        (D) TOPOLOGY: linear (ii) MOLECULE TYPE: DNA (oligonucleotide)

(xi) SEQUENCE DESCRIPTION: SEQ ID NO: 28:

AAACCCAATC CACATCM                                                    17

(2) INFORMATION FOR SEQ ID NO: 29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 29:

MMACNCANNC CACANNM                                                    17

(2) INFORMATION FOR SEQ ID NO: 30:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 30:

TTGGGTACCA C                                                          11

(2) INFORMATION FOR SEQ ID NO: 31:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 31:

TTGAAMACCA C                                                          11

(2) INFORMATION FOR SEQ ID NO: 32:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 32:

ACAGAAATGG A                                                          11

(2) INFORMATION FOR SEQ ID NO: 33:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 33:

AGAGRATDGG R                                                              11

(2) INFORMATION FOR SEQ ID NO: 34:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (oligonucleotide)

(xi) SEQUENCE DESCRIPTION: SEQ ID NO: 34:

ASAGRRADGG A                                                              11

(2) INFORMATION FOR SEQ ID NO: 35:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (oligonucleotide)

(xi) SEQUENCE DESCRIPTION: SEQ ID NO: 35:

ACAGGGRRGG A                                                              11

(2) INFORMATION FOR SEQ ID NO: 36:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (oligonucleotide)

(xi) SEQUENCE DESCRIPTION: SEQ ID NO: 36:

CTGGGGGGTA T                                                              11

(2) INFORMATION FOR SEQ ID NO: 37:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (oligonucleotide)

(xi) SEQUENCE DESCRIPTION: SEQ ID NO: 37:

CTGGCCSGTG T                                                              11

(2) INFORMATION FOR SEQ ID NO: 38:

(i) SEQUENCE CHARACTERISTICS:
              (A) LENGTH: 11 base pairs
              (B) TYPE: nucleic acid
              (C) STRANDEDNESS: single
              (D) TOPOLOGY: linear (ii) MOLECULE TYPE: DNA (oligonucleotide)

(xi) SEQUENCE DESCRIPTION: SEQ ID NO: 38:

CTGGGCGGTA T                                                              11

(2) INFORMATION FOR SEQ ID NO: 39:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 39:

CTGGCACGTG T                                                                11

56

56

COMPUTER-AIDED VISUALIZATION AND ANALYSIS SYSTEM FOR SEQUENCE EVALUATION

This is a Continuation of prior application Ser. No. 09/158,765, filed Sep. 23, 1998, now issued as U.S. Pat. No. 6,242,180, which is a continuation of prior application Ser. No. 08/531,137, filed Oct. 16, 1995, now issued as U.S. Pat. No. 5,974,164, which is a continuation-in-part of U.S. patent application Ser. No. 08/327,525, filed Oct. 21, 1994, now issued as U.S. Pat. No. 5,795,716.

GOVERNMENT RIGHTS NOTICE

Portions of the material in this specification arose in the course of or under contract nos. 92ER81275 (SBIR) between Affymetrix, Inc. and the Department of Energy and/or H600813-1, -2 between Affymetrix, Inc. and the National Institutes of Health.

COPYRIGHT NOTICE

A portion of the disclosure of this patent document contains material which is subject to copyright protection. The copyright owner has no objection to the xeroxographic reproduction by anyone of the patent document or the patent disclosure in exactly the form it appears in the Patent and Trademark Office patent file or records, but otherwise reserves all copyright rights whatsoever.

MICROFICHE APPENDIX

Microfiche Appendices A to E comprising five (5) sheets, totaling 272 frames are included herewith.

BACKGROUND OF THE INVENTION

The present invention relates to the field of computer systems. More specifically, the present invention relates to computer systems for visualizing biological sequences, as well as for evaluating and comparing biological sequences.

Devices and computer systems for forming and using arrays of materials on a substrate are known. For example, PCT applications WO92/10588 and 95/11995, incorporated herein by reference for all purposes, describe techniques for sequencing or sequence checking nucleic acids and other materials. Arrays for performing these operations may be formed in arrays according to the methods of, for example, the pioneering techniques disclosed in U.S. Pat. Nos. 5,445,934 and 5,384,261, and U.S. patent application Ser. No. 08/249,188, each incorporated herein by reference for all purposes.

According to one aspect of the techniques described therein, an array of nucleic acid probes is fabricated at known locations on a chip or substrate. A labeled nucleic acid is then brought into contact with the chip and a scanner generates an image file (also called a cell file) indicating the locations where the labeled nucleic acids bound to the chip. Based upon the image file and identities of the probes at specific locations, it becomes possible to extract information such as the monomer sequence of DNA or RNA. Such systems have been used to form, for example, arrays of DNA that may be used to study and detect mutations relevant to cystic fibrosis, the P53 gene (relevant to certain cancers), HIV, and other genetic characteristics.

Improved computer systems and methods are needed to evaluate, analyze, and process the vast amount of information now used and made available by these pioneering technologies.

SUMMARY OF THE INVENTION

An improved computer-aided system for visualizing and determining the sequence of nucleic acids is disclosed. The computer system provides, among other things, improved methods of analyzing fluorescent image files of a chip containing hybridized nucleic acid probes in order to call bases in sample nucleic acid sequences.

According to one aspect of the invention, a computer system is used to identify an unknown base in a sample nucleic acid sequence by the steps of:

inputting multiple probe intensities, each of the probe intensities being associated with a nucleic acid probe;

the computer system comparing the multiple probe intensities where each of the probe intensities is substantially proportional to a nucleic acid probe hybridizing with at least one nucleic acid sequence; and calling the unknown base according to the results of the comparison of the multiple probe intensities.

According to one specific aspect of the invention, a higher probe intensity is compared to a lower probe intensity to call the unknown base. According to another specific aspect of the invention, probe intensities of a sample sequence are compared to probe intensities of a reference sequence. According to yet another specific aspect of the invention, probe intensities of a sample sequence are compared to statistics about probe intensities of a reference sequence from multiple experiments.

According to another aspect of the invention, a method is disclosed of processing reference and sample nucleic acid sequences to reduce the variations between the experiments by the steps of:

providing a plurality of nucleic acid probes;

labeling the reference nucleic acid sequence with a first marker;

labeling the sample nucleic acid sequence with a second marker; and hybridizing the labeled reference and sample nucleic acid sequences at the same time.

According to another aspect of the invention, a computer system is used to identify mutations in a sample nucleic acid sequence by the steps of:

inputting a first set of probe intensities, each of the probe intensities in said first set being associated with a nucleic acid probe and substantially proportional to the associated nucleic acid probe hybridizing with a reference nucleic acid sequence;

inputting a second set of probe intensities, each of the probe intensities in said first set being associated with a nucleic acid probe and substantially proportional to the associated nucleic acid probe hybridizing with said sample sequence;

the computer system comparing probe intensities in the first set to probe intensities in the second set to select hybridization regions where the probe intensities in the first and second sets differ; and identifying mutations according to characteristics of the selected regions.

According to yet another aspect of the invention, a computer system is used for comparative analysis and visualization of multiple sequences by the steps of:

displaying at least one reference sequence in a first area on a display device; and displaying at least one sample sequence in a second area on said display device;

whereby a user is capable of visually comparing the multiple sequences.

A further understanding of the nature and advantages of the inventions herein may be realized by reference to the remaining portions of the specification and the attached drawings.

BRIEF DESCRIPTION OF THE DRAWINGS

FIG. 10A illustrates the high level flow of one implementation of the reference method and FIG. 10B shows an analysis table for use with the reference method;

FIG. 11B shows a data table for use with the reference method;

FIG. 19 illustrates the intensity ratio method correctly calling a mutation in solutions with varying concentrations;

FIG. 21 illustrates the output of the ViewSeq™ program with four pretreatment samples and four post treatment samples.

DESCRIPTION OF THE PREFERRED EMBODIMENT

Contents

I. General
II. Intensity Ratio Method
III. Reference Method
IV. Statistical Method
V. Pooling Processing
VI. Comparative Analysis
VII. Examples
VIII. Appendices I. General In the description that follows, the present invention will be described in reference to a Sun Workstation in a UNIX environment. The present invention, however, is not limited to any particular hardware or operating system environment. Instead, those skilled in the art will find that the systems and methods of the present invention may be advantageously applied to a variety of systems, including IBM personal computers running MS-DOS or Microsoft Windows. Therefore, the following description of specific systems are for purposes of illustration and not limitation.

Figure 1:
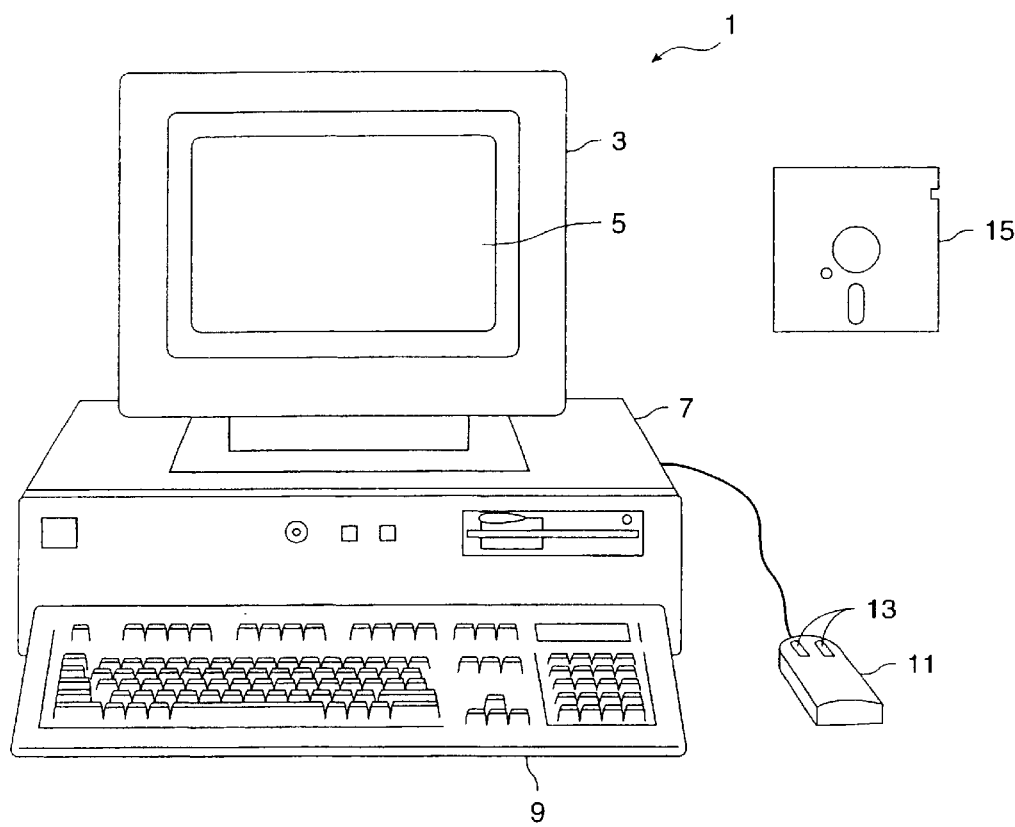
FIG. 1 illustrates an example of a computer system used to execute the software of the present invention.

FIG. 1 illustrates an example of a computer system used to execute the software of the present invention. FIG. 1 shows a computer system 1 which includes a monitor 3, screen 5, cabinet 7, keyboard 9, and mouse 11. Mouse 11 may have one or more buttons such as mouse buttons 13. Cabinet 7 houses a floppy disk drive 14 and a hard drive (not shown) that may be utilized to store and retrieve software programs incorporating the present invention. Although a floppy disk 15 is shown as the removable media, other removable tangible media including CD-ROM, flash memory and tape may be utilized. Cabinet 7 also houses familiar computer components (not shown) such as a processor, memory, and the like.

Figure 2:
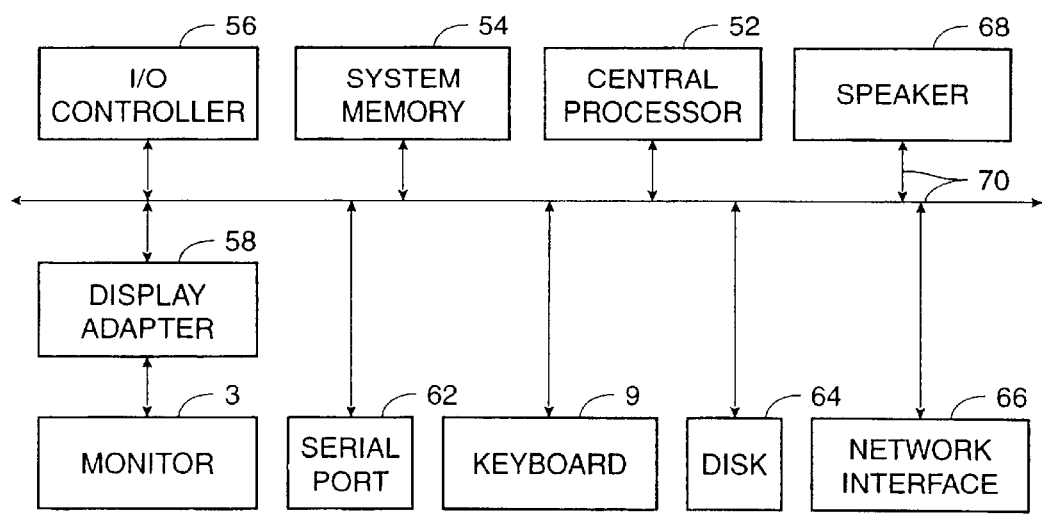
FIG. 2 shows a system block diagram of a typical computer system used to execute the software of the present invention.

FIG. 2 shows a system block diagram of computer system 1 used to execute the software of the present invention. As in FIG. 1, computer system 1 includes monitor 3 and keyboard 9. Computer system 1 further includes subsystems such as a central processor 52, system memory 54, I/O controller 56, display adapter 58, serial port 62, disk 64, network interface 66, and speaker 68. Disk 64 is representative of an internal hard drive, floppy drive, CD-ROM, flash memory, tape, or any other storage medium. Other computer systems suitable for use with the present invention may include additional or fewer subsystems. For example, another computer system could include more than one processor 52 (i.e., a multi-processor system) or memory cache.

Arrows such as 70 represent the system bus architecture of computer system 1. However, these arrows are illustrative of any interconnection scheme serving to link the subsystems. For example, speaker 68 could be connected to the other subsystems through a port or have an internal direct connection to central processor 52. Computer system 1 shown in FIG. 2 is but an example of a computer system suitable for use with the present invention. Other configurations of subsystems suitable for use with the present invention will be readily apparent to one of ordinary skill in the art.

The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. The oligonucleotide probes on the DNA probe array are used to detect complementary nucleic acid sequences in a sample nucleic acid of interest (the "target" nucleic acid).

The present invention provides methods of analyzing hybridization intensity files for a chip containing hybridized nucleic acid probes. In a representative embodiment, the files represent fluorescence data from a biological array, but the files may also represent other data such as radioactive intensity data or large molecule detection data. Therefore, the present invention is not limited to analyzing fluorescent measurements of hybridizations but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. patent application Ser. No. 08/249,188 which has been incorporated by reference for all purposes. However, the present invention may be used separately from the overall system for analyzing data generated by such systems.

Figure 3:
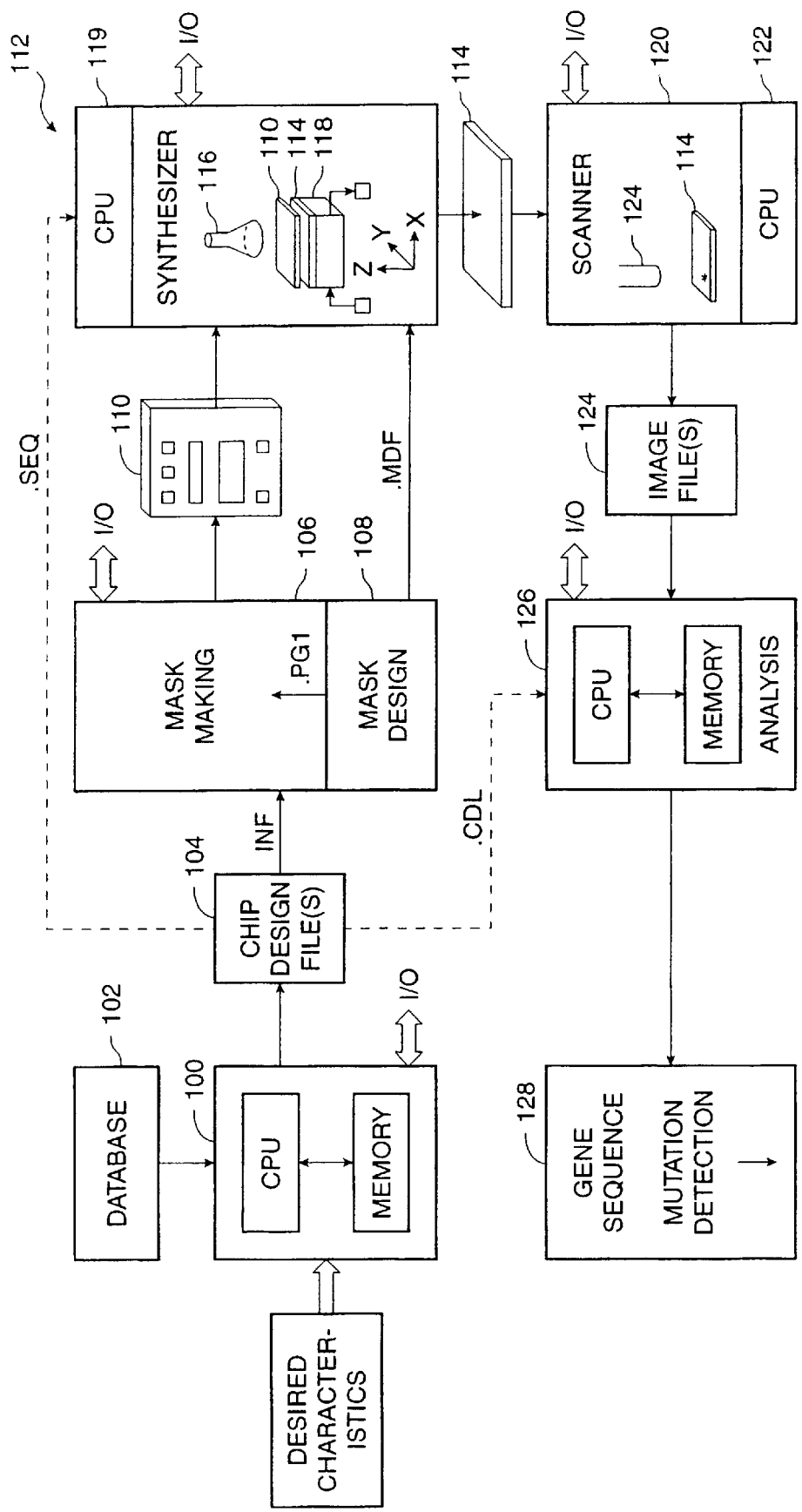
FIG. 3 illustrates an overall system for forming and analyzing arrays of biological materials such as DNA or RNA.

FIG. 3 illustrates a computerized system for forming and analyzing arrays of biological materials such as RNA or DNA. A computer 100 is used to design arrays of biological polymers such as RNA or DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site, but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical reagents are directed through flow cell 118 for coupling to deprotected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked receptors. The receptors may or may not be complementary to one or more of the molecules on the substrate. The receptors are marked with a label such as a fluorescein label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the locations where labeled receptor (*) has bound to the substrate. The output of scanner 120 is an image file(s) 124 indicating, in the case of fluorescein labeled receptor, the fluorescence intensity (photon counts or other related measurements, such as voltage) as a function of position on the substrate. Since higher photon counts will be observed where the labeled receptor has bound more strongly to the array of polymers, and since the monomer sequence of the polymers on the substrate is known as a function of position, it becomes possible to determine the sequence(s) of polymer(s) on the substrate that are complementary to the receptor.

The image file 124 is provided as input to an analysis system 126 that incorporates the visualization and analysis methods of the present invention. Again, the analysis system may be any one of a wide variety of computer system(s), but in a preferred embodiment the analysis system is based on a Sun Workstation or equivalent. The present invention provides various methods of analyzing the chip design files and the image files, providing appropriate output 128. The present invention may further be used to identify specific mutations in a receptor such as DNA or RNA.

Figure 4:
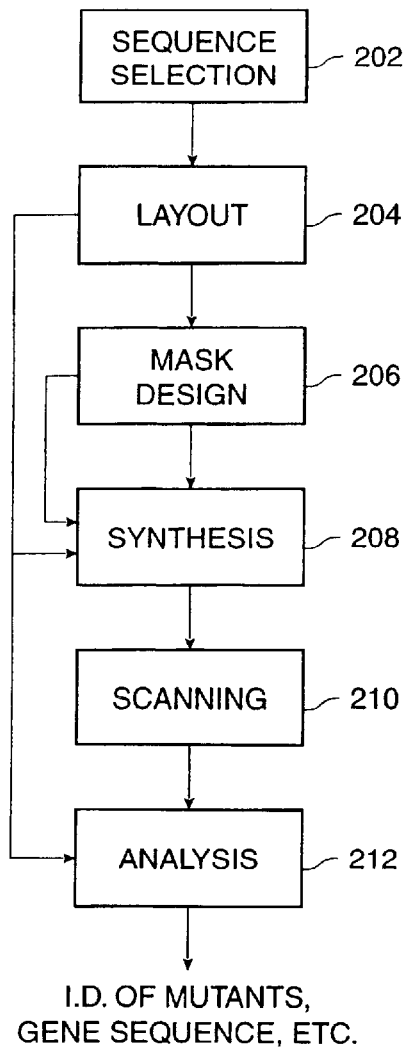
FIG. 4 is an illustration of the software for the overall system.

FIG. 4 provides a simplified illustration of the overall software system used in the operation of one embodiment of the invention. As shown in FIG. 4, in some cases (such as sequence checking systems) the system first identifies the genetic sequence(s) or targets that would be of interest in a particular analysis at step 202. The sequences of interest may, for example, be normal or mutant portions of a gene, genes that identify heredity, or provide forensic information, or be all possible n-mers (where n represents the length of the nucleic acid). Sequence selection may be provided via manual input of text files or may be from external sources such as GenBank. At step 204 the system evaluates the gene to determine or assist the user in determining which probes would be desirable on the chip, and provides an appropriate "layout" on the chip for the probes. The chip usually includes probes that are complementary to a reference nucleic acid sequence which has a known sequence. A wild-type probe is a probe that will ideally hybridize with the reference sequence and thus a wild-type gene (also called the chip wild-type) would ideally hybridize with wild-type probes on the chip. The target sequence is substantially similar to the reference sequence except for the presence of mutations, insertions, deletions, and the like. The layout implements desired characteristics such as arrangement on the chip that permits "reading" of genetic sequence and/or minimization of edge effects, ease of synthesis, and the like.

Figure 5:
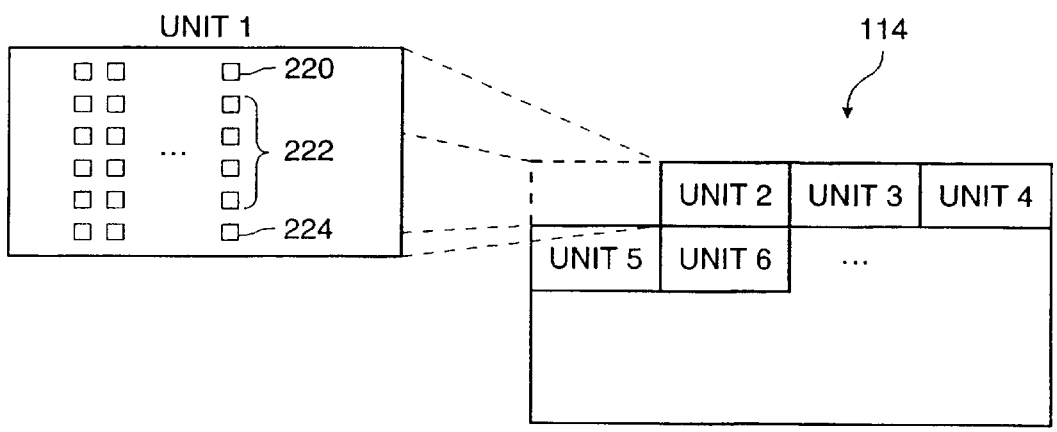
FIG. 5 illustrates the global layout of a chip formed in the overall system.

FIG. 5 illustrates the global layout of a chip in a particular embodiment used for sequence checking applications. Chip 114 is composed of multiple units where each unit may contain different tilings for the chip wild-type sequence. Unit 1 is shown in greater detail and shows that each unit is composed of multiple cells which are areas on the chip that may contain probes. Conceptually, each unit is composed of multiple sets of related cells. As used herein, the term cell refers to a region on a substrate that contains many copies of a molecule or molecules of interest. Each unit is composed of multiple cells that may be placed in rows (or "lanes") and columns. In one embodiment, a set of five related cells includes the following: a wild-type cell 220, "mutation" cells 222, and a "blank" cell 224. Cell 220 contains a wild-type probe that is the complement of a portion of the wild-type sequence. Cells 222 contain "mutation" probes for the wild-type sequence. For example, if the wild-type probe is 3'-ACGT, the probes 3'-ACAT, 3'-ACCT, 3'-ACGT, and 3'-ACTT may be the "mutation" probes. Cell 224 is the "blank" cell because it contains no probes (also called the "blank" probe). As the blank cell contains no probes, labeled receptors should not bind to the chip in this area. Thus, the blank cell provides an area that can be used to measure the background intensity.

In one embodiment, numerous tiling processes are available including sequence tiling, block tiling, and opt-tiling, as described below. Of course a wide range of layout strategies may be used according to the invention herein, without departing from the scope of the invention. For example, the probes may be tiled on a substrate in an apparently random fashion where a computer system is utilized to keep track of the probe locations and correlate the data obtained from the substrate.

Opt-tiling is the process of tiling additional probes for suspected mutations. As a simple example of opt-tiling, suppose the wild-type target sequence is 5'-ACGT ATGCA-3' and it is suspected that a mutant sequence has a possible T base mutation at the underlined base position. Suppose further that the chip will be synthesized with a "4×3" tiling strategy, meaning that probes of four monomers are used and that the monomers in position 3, counting left to right, of the probe are varied.

In opt-tiling, extra probes are tiled for each suspected mutation. The extra probes are tiled as if the mutation base is a wild-type base. The following shows the probes that may be generated for this example:

TABLE 1

Probe Sequences (From 3'-end)
4 × 3 Opt-Tiling

| Wild   | TGCA | GCAT | CATA | ATAC | TACG |
| A sub. | TGAA | GCAT | CAAA | ATAC | TAAG |
| C sub. | TGCA | GCCT | CACA | ATCC | TACG |
| G sub. | TGGA | GCGT | CAGA | ATGC | TAGG |
| T sub. | TGTA | GCTT | CATA | ATTC | TATG |
| Wild   | TGCA | GCAA | CAAA | AAAC | AACG |
| A sub. | TGAA | GCAA | CAAA | AAAC | AAAG |
| C sub. | TGCA | GCCA | CACA | AACC | AACG |
| G sub. | TGGA | GCGA | CAGA | AAGC | AAGG |
| T sub. | TGTA | GCTA | CATA | AATC | AATG |

In the first "chip" above, the top row of the probes (along with one probe below each of the four wild-type probes) should bind to the target DNA sequence. However, if the target sequence has a T base mutation as suspected, the labeled mutant sequence will not bind that strongly to the probes in the columns around column 3. For example, the mutant receptor that could bind with the probes in column 2 is 5'-CGTT which may not bind that strongly to any of the probes in column 2 because there are T bases at the ends of the receptor and probes (i.e., not complementary). This often results in a relatively dark scanned area around a mutation.

Opt-tiling generates the second "chip" above to handle the suspected mutation as a wild-type base. Thus, the mutant receptor 5'-CGTT should bind strongly to the wild-type probe of column 2 (along with one probe below) and the mutation can be further detected.

Again referring to FIG. 4, at step 206 the masks for the synthesis are designed. At step 208 the software utilizes the mask design and layout information to make the DNA or other polymer chips. This software 208 will control relative translation of a substrate and the mask, the flow of desired reagents through a flow cell, the synthesis temperature of the flow cell, and other parameters. At step 210, another piece of software is used in scanning a chip thus synthesized and exposed to a labeled receptor. The software controls the scanning of the chip, and stores the data thus obtained in a file that may later be utilized to extract sequence information.

At step 212 a computer system according to the present invention utilizes the layout information and the fluorescence information to evaluate the hybridized nucleic acid probes on the chip. Among the important pieces of information obtained from probe arrays are the identification of mutant receptors and determination of genetic sequence of a particular receptor.

Figures 6, 7, 8:
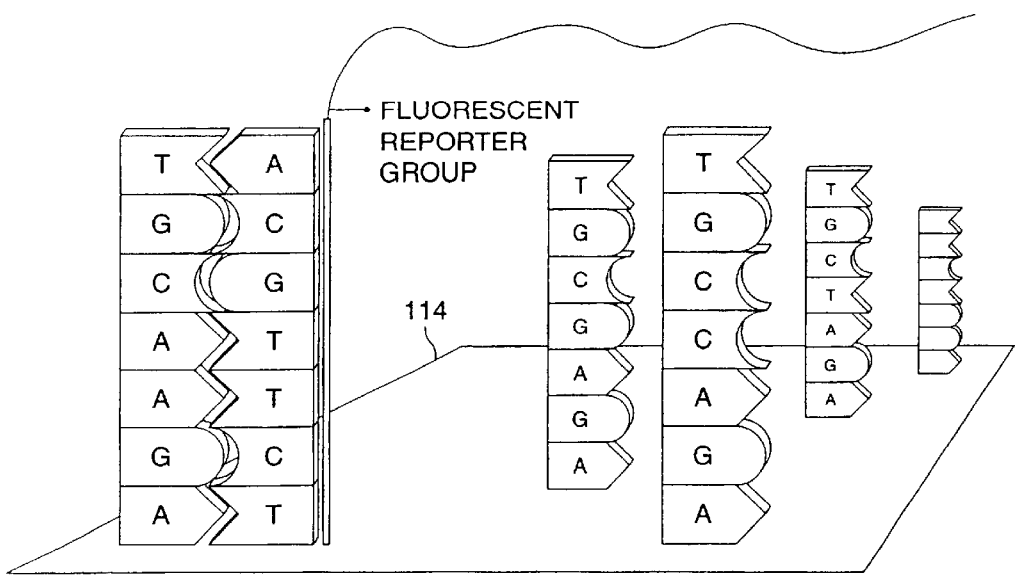
FIG. 6 illustrates conceptually the binding of probes on chips.
FIG. 7 illustrates probes arranged in lanes on a chip.
FIG. 8 illustrates a hybridization pattern of a target on a chip with a reference sequence as in FIG. 7.

FIG. 6 illustrates the binding of a particular target DNA to an array of DNA probes 114. As shown in this simple example, the following probes are formed in the array (only one probe is shown for the wild-type probe):

```
3'-AGAACGT
  AGACCGT
  AGAGCGT
  AGATCGT
     .
     .
     .
```

As shown, the set of probes differ by only one base so the probes are designed to determine the identity of the base at that position in the nucleic acid sequence.

When a fluorescein-labeled (or otherwise marked) target with the sequence 5'-TCTTGCA is exposed to the array, it is complementary only to the probe 3'-AGAACGT, and fluorescein will be primarily found on the surface of the chip where 3'-AGAACGT is located. Thus, for each set of probes that differ by only one base, the image file will contain four fluorescence intensities, one for each probe. Each fluorescence intensity can therefore be associated with the base of each probe that is different from the other probes. Additionally, the image file will contain a "blank" cell which can be used as the fluorescence intensity of the background. By analyzing the five fluorescence intensities associated with a specific base location, it becomes possible to extract sequence information from such arrays using the methods of the invention disclosed herein.

FIG. 7 illustrates probes arranged in lanes on a chip. A reference sequence is shown with five interrogation positions marked with number subscripts. An interrogation position is a base position in the reference sequence where the target sequence may contain a mutation or otherwise differ from the reference sequence. The chip may contain five probe cells that correspond to each interrogation position. Each probe cell contains a set of probes that have a common base at the interrogation position. For example, at the first interrogation position, $I_1$, the reference sequence has a base T. The wild-type probe for this interrogation position is 3'-TGAC where the base A in the probe is complementary to the base at the interrogation position in the reference sequence.

Similarly, there are four "mutant" probe cells for the first interrogation position, $I_1$. The four mutant probes are 3'-TGAC, 3'-TGCC, 3'-TGGC, and 3'-TGTC. Each of the four mutant probes vary by a single base at the interrogation position. As shown, the wild-type and mutant probes are arranged in lanes on the chip. One of the mutant probes (in this case 3'-TGAC) is identical to the wild-type probe and therefore does not evidence a mutation. However, the redundancy gives a visual indication of mutations as will be seen in FIG. 8.

Still referring to FIG. 7, the chip contains wild-type and mutant probes for each of the other interrogation positions $I_2$–$I_5$. In each case, the wild-type probe is equivalent to one of the mutant probes.

FIG. 8 illustrates a hybridization pattern of a target on a chip with a reference sequence as in FIG. 7. The reference sequence is shown along the top of the chip for comparison. The chip includes a WT-lane (wild-type), an A-lane, a C-lane, a G-lane, and a T-lane (or U). Each lane is a row of cells containing probes. The cells in the WT-lane contain probes that are complementary to the reference sequence. The cells in the A-, C-, G-, and T-lanes contain probes that are complementary to the reference sequence except that the named base is at the interrogation position.

In one embodiment, the hybridization of probes in a cell is determined by the fluorescent intensity (e.g., photon counts) of the cell resulting from the binding of marked target sequences. The fluorescent intensity may vary greatly among cells. For simplicity, FIG. 8 shows a high degree of hybridization by a cell containing a darkened area. The WT-lane allows a simple visual indication that there is a mutation at interrogation position $I_4$ because the wild-type cell is not dark at that position. The cell in the C-lane is darkened which indicates that the mutation is from T→G (mutant probe cells are complementary so the C-cell indicates a G mutation).

In practice, the fluorescent intensities of cells near an interrogation position having a mutation are relatively dark creating "dark regions" around a mutation. The lower fluorescent intensities result because the cells at interrogation positions near a mutation do not contain probes that are perfectly complementary to the target sequence; thus, the hybridization of these probes with the target sequence is lower. For example, the relative intensity of the cells at interrogation positions $I_{13}$ and $I_5$ may be relatively low because none of the probes therein are complementary to the target sequence.

For ease of reference, one may call bases by assigning the bases the following codes:

| Code | Group | Meaning |
| --- | --- | --- |
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G, or T(U) | Insufficient intensity to call |

-continued

| Code | Group | Meaning |
| --- | --- | --- |
| X | A, C, G, or T(U) | Insufficient discrimination to call |

Most of the codes conform to the IUPAC standard. However, code N has been redefined and code X has been added.

II. Intensity Ratio Method

The intensity ratio method is a method of calling bases in a sample nucleic acid sequence. The intensity ratio method is most accurate when there is good discrimination between the fluorescence intensities of hybrid matches and hybrid mismatches. If there is insufficient discrimination, the intensity ratio method assigns a corresponding ambiguity code to the unknown base.

For simplicity, the intensity ratio method will be described as being used to identify one unknown base in a sample nucleic acid sequence. In practice, the method is used to identify many or all the bases in a nucleic acid sequence.

The unknown base will be identified by evaluation of up to four mutation probes and a "blank" cell, which is a location where a labeled receptor should not bind to the chip since no probe is present. For example, suppose a DNA sequence of interest or target sequence contains the sequence 5'-AGAACCTGC-3' with a possible mutation at the underlined base position. Suppose that 5-mer probes are to be synthesized for the target sequence. A representative wild-type probe of 5'-TTGGA is complementary to the region of the sequence around the possible mutation. The "mutation" probes will be the same as the wild-type probe except for a different base at the third position as follows: 3'-TTAGA, 3'-TTCGA, 3'-TTGGA, and 3'-TTTGA.

If the fluorescently marked sample sequence is exposed to the above four mutation probes, the intensity should be highest for the probe that binds most strongly to the sample sequence. Therefore, if the probe 3'-TTTGA shows the highest intensity, the unknown base in the sample will generally be called an A mutation because the probes are complementary to the sample sequence.

The mutation probes are identical to the wild-type probes except that they each contain one of the four A, C, G, or T "mutations" for the unknown base. Although one of the "mutation" probes will be identical to the wild-type probe, such redundant probes are intentionally synthesized for quality control and design consistency.

The identity of the unknown base is preferably determined by evaluating the relative fluorescence intensities of up to four of the mutation probes, and the "blank" cell. Because each mutation probe is identifiable by the mutation base, a mutation probe's intensity will be referred to as the "base intensity" of the mutation base.

As a simple example of the intensity ratio method, suppose a gene of interest (target) is an HIV protease gene with the sequence 5'-ATGTGGACAGTTGTA-3' (SEQ ID NO:1). Suppose further that a sample sequence is suspected to have the same sequence as the target sequence except for a mutation of base C to base T at the underlined base position. Although hundreds of probes may be synthesized on the chip, the complementary mutation probes synthesized to detect a mutation in the sample sequence at the suspected mutation position may be as follows:

```
3'-TATC
3'-TCTC
3'-TGTC            (wild-type)
3'-TTTC
```

The mutation probe 3'-TGTC is also the wild-type probe as it should bind most strongly with the target sequence.

After the sample sequence is labeled, hybridized on the chip, and scanned, suppose the following fluorescence intensities were obtained:

```
3'-TATC         -> 45
3'-TCTC         -> 8
3'-TGTC         -> 32
3'-TTTC         -> 12
``` where the intensity is measured by the photon count detected by the scanner. The "blank" cell had a fluorescence intensity of 2. The photon counts in the examples herein are representative (not actual data) and provided for illustration purposes. In practice, the actual photon counts will vary greatly depending on the experiment parameters and the scanner utilized.

Although each fluorescence intensity is from a probe, the probes may be characterized by their unique mutation base so the bases may be said to have the following intensities:

A→45
C→8
G→32
T→12

Thus, base A will be described as having an intensity of 45, which corresponds to the intensity of the mutation probe with the mutation base A.

Initially, each mutation base intensity is reduced by the background or "blank" cell intensity. This is done as follows:

A→45−2=43
C→8−2=6
G→32−2=30
T→12−2=10

Then, the base intensities are sorted in descending order of intensity. The above bases would be sorted as follows:

A→43
G→30
T→10
C→6

Next, the highest intensity base is compared to the second highest intensity base. Thus, the ratio of the intensity of base A to the intensity of base G is calculated as follows: A:G=43/30=1.4. The ratio A:G is then compared to a predetermined ratio cutoff, which is a number that specifies the ratio required to identify the unknown base. For example, if the ratio cutoff is 1.2, the ratio A:G is greater than the ratio cutoff (1.4>1.2) and the unknown base is called by the mutation probe containing the mutation A. As probes are complementary to the sample sequence, the sample sequence is called as having a mutation T, resulting in a called sample sequence of 5'-ATGTGGATAGTTGTA-3' (SEQ ID NO:2).

As another example, suppose everything else is the same as in the previous example except that the sorted background adjusted intensities were as follows:

C→42
A→40
G→10
T→8

The ratio of the highest intensity base to the second highest intensity base (C:A) is 1.05. Because this ratio is not greater than the ratio cutoff of 1.2, the unknown base will be called as being ambiguously one of two or more bases as follows.

The second highest intensity base is then compared to the third highest base. The ratio of A:G is 4. The ratio of A:G is then compared to the ratio cutoff of 1.2. As the ratio A:G is greater than the ratio cutoff (4>1.2), the unknown base is called by the mutation probes containing the mutations C or A. As probes are complementary to the sample sequence, the sample sequence is called as having either a mutation G or T, resulting in a sample sequence of 5'-ATGTGGAKAGTTGTA-3' (SEQ ID NO:3) where K is the IUPAC code for G or T(U).

The ratio cutoff in the previous examples was equal to 1.2. However, the ratio cutoff will generally need to be adjusted to produce optimal results for the specific chip design and wild-type target. Also, although the ratio cutoff used has been the same for each ratio comparison, the ratio cutoff may vary depending on whether the ratio comparisons involve the highest, second highest, third highest, etc. intensity base.

Figure 9:
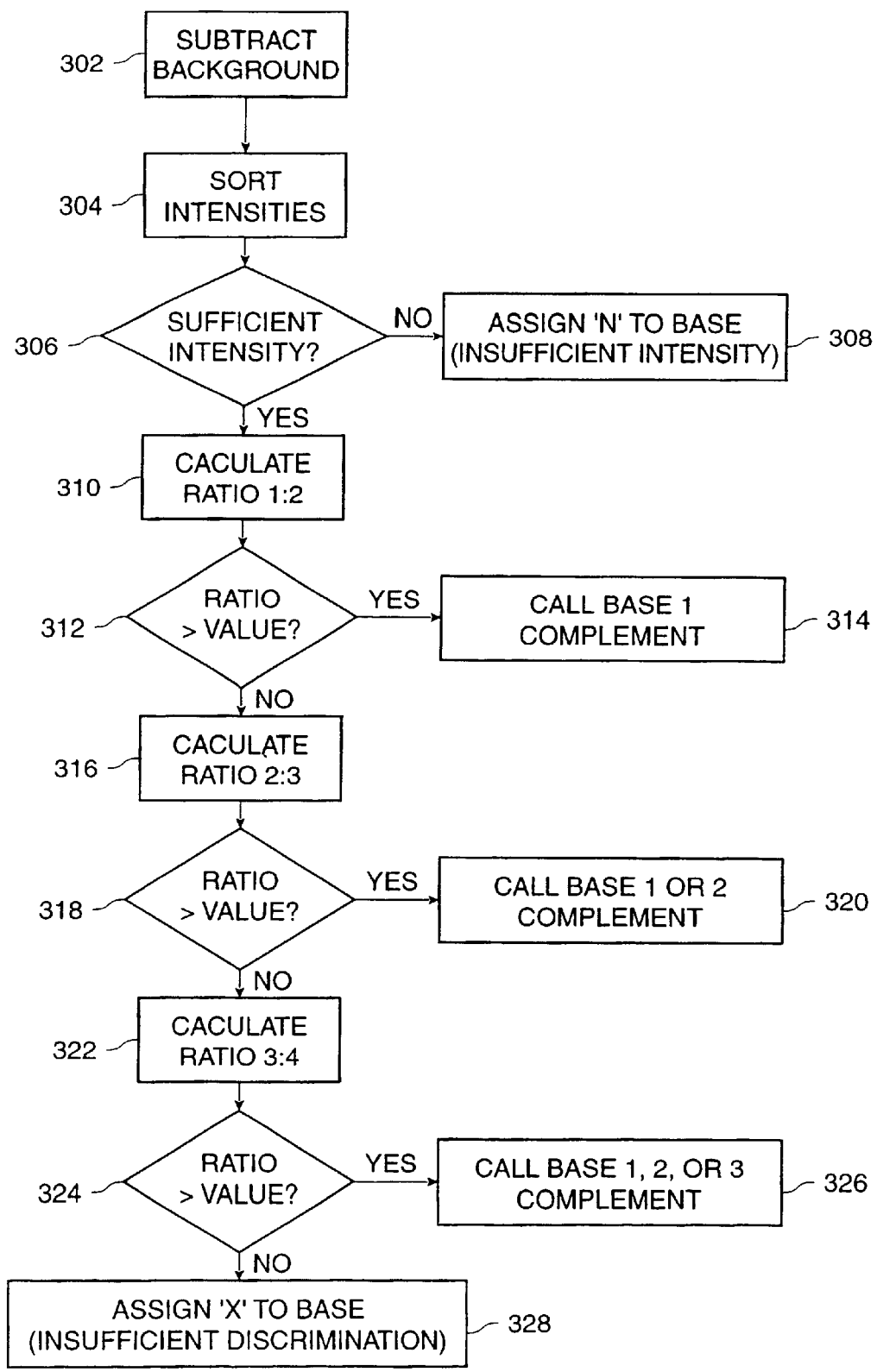
FIG. 9 illustrates the high level flow of the intensity ratio method.

FIG. 9 illustrates the high level flow of the intensity ratio method. At step 302 the four base intensities are adjusted by subtracting the background or "blank" cell intensity from each base intensity. Preferably, if a base intensity is then less than or equal to zero, the base intensity is set equal to a small positive number to prevent division by zero or negative numbers in future calculations.

At step 304 the base intensities are sorted by intensity. Each base is then associated with a number from 1 to 4. The base with the highest intensity is 1, second highest 2, third highest 3, and fourth highest 4. Thus, the intensity of base 1≧base 2≧base 3≧base 4.

At step 306 the highest intensity base (base 1) is checked to see if it has sufficient intensity to call the unknown base. The intensity is checked by determining if the intensity of base 1 is greater than a predetermined background difference cutoff. The background difference cutoff is a number that specifies the intensity a base intensity must be over the background intensity in order to correctly call the unknown base. Thus, the background adjusted base intensity must be greater than the background difference cutoff or the unknown is not callable.

If the intensity of base 1 is not greater than the background difference cutoff, the unknown base is assigned the code N (insufficient intensity) as shown at step 308. Otherwise, the ratio of the intensity of base 1 to base 2 is calculated as shown at step 310.

At step 312 the ratio of intensity of bases 1:2 is compared to the ratio cutoff. If the ratio 1:2 is greater than the ratio cutoff, the unknown base is called as the complement of the highest intensity base (base 1) as shown at step 314. Otherwise, the ratio of the intensity of base 2 to base 3 is calculated as shown at step 316.

At step 318 the ratio of intensity of bases 2:3 is compared to the ratio cutoff. If the ratio 2:3 is greater than the ratio cutoff, the unknown base is called as being an ambiguity code specifying the complements of the highest or second highest intensity bases (base 1 or 2) as shown at step 320. Otherwise, the ratio of the intensity of base 3 to base 4 is calculated as shown at step 322.

At step 324 the ratio of intensity of bases 3:4 is compared to the ratio cutoff. If the ratio 3:4 is greater than the ratio cutoff, the unknown base is called as being an ambiguity code specifying the complements of the highest, second highest, or third highest bases (base 1, 2 or 3) as shown at step 326. Otherwise, the unknown base is assigned the code X (insufficient discrimination) as shown at step 328.

The advantage of the intensity ratio method is that it is very accurate when there is good discrimination between the fluorescence intensities of hybrid matches and hybrid mismatches. However, if the base corresponding to a correct hybrid gives a lower intensity than a mismatch (e.g., as a result of cross-hybridization), incorrect identification of the base will result. For this reason, however, the method is useful for comparative assessment of hybridization quality and as an indicator of sequence-specific problem spots. For example, the intensity ratio method has been used to determine that ambiguities and miscalls tend to be very different from sequence to sequence, and reflect predominantly the composition and repetitiveness of the sequence. It has also been used to assess improvements obtained by varying hybridization conditions, sample preparation, and post-hybridization treatments (e.g., RNase treatment).

III. Reference Method

The reference method is a method of calling bases in a sample nucleic acid sequence. The reference method depends very little on discrimination between the fluorescence intensities of hybrid matches and hybrid mismatches, and therefore is much less sensitive to cross-hybridization. The method compares the probe intensities of a reference sequence to the probe intensities of a sample sequence. Any significant changes are flagged as possible mutations. There are two implementations of the reference method disclosed herein.

For simplicity, the reference method will be described as being used to identify one unknown base in a sample nucleic acid sequence. In practice, the method is used to identify many or all the bases in a nucleic acid sequence.

The unknown base will be called by comparing the probe intensities of a reference sequence to the probe intensities of a sample sequence. Preferably, the probe intensities of the reference sequence and the sample sequence are from chips having the same chip wild-type. However, the reference sequence may or may not be exactly the same as the chip wild-type, as it may have mutations.

The bases at the same position in the reference and sample sequences will each be associated with up to four mutation probes and a "blank" cell. The unknown base in the sample sequence is called by comparing probe intensities of the sample sequence to probe intensities of the reference sequence. For example, suppose the chip wild-type contains the sequence 5'-AGACCTTGC-3' and it is suspected that the sample has a possible mutation at the underlined base position, which is the unknown base that will be called by the reference method. The "mutation" probes for the sample sequence may be as follows; 3'-GAAA, 3'-GCAA, 3'-GGAA, and 3'-GTAA, where 3'-GGAA is the wild-type probe.

Suppose further that a reference sequence, which differs from the chip wild-type by one base mutation, has the sequence 5'-AGACATTGC-3' where the mutation base is underlined. The "mutation" probes for the reference sequence may be as follows: 3'-TGAAA, 3'-TGCAA, 3'-TGGAA, and 3'-TGTAA, where 3'-TGTAA is the reference wild-type probe since the reference sequence is known. Although generally the sample and reference sequences were tiled with the same chip wild-type, this is not required, and the tiling methods do not have to be identical as shown by the use of two probe lengths in the example. Thus, the unknown base will be called by comparing the "mutation" probes of the sample sequence to the "mutation" probes of the reference sequence. As before, because each mutation probe is identifiable by the mutation base, the mutation probes' intensities will be referred to as the "base intensities" of their respective mutation bases.

As a simple example of one implementation of the reference method, suppose a gene of interest (target) has the sequence 5'-AAAACTGAAAA-3' (SEQ ID NO:4). Suppose a reference sequence has the sequence 5'-AAAAC̲CGAAAA-3' (SEQ ID NO:5), which differs from the target sequence by the underlined base. The reference sequence is marked and exposed to probes on a chip with the target sequence being the chip wild-type. Suppose further that a sample sequence is suspected to have the same sequence as the target sequence except for a mutation at the underlined base position in 5'-AAAAC̲TGAAAA-3' (SEQ ID NO:4). The sample sequence is also marked and exposed to probes on a chip with the target sequence being the chip wild-type. After hybridization and scanning, the following probe intensities (not actual data) were found for the respective complementary probes:

| Reference | Sample |
|---|---|
| 3'-TGAC –> 12 | 3'-GACT –> 11 |
| 3'-TGCC –> 9 | 3'-GCCT –> 30 |
| 3'-TGGC –> 80 | 3'-GGCT –> 60 |
| 3'-TGTC –> 15 | 3'-GTCT –> 6 |

Although each fluorescence intensity is from a probe, the probes may be identified by their unique mutation base so the bases may be said to have the following intensities:

| Reference | Sample |
|---|---|
| A –> 12 | A –> 11 |
| C –> 9 | C –> 30 |
| G –> 80 | G –> 60 |
| T –> 15 | T –> 6 |

Thus, base A of the reference sequence will be described as having an intensity of 12, which corresponds to the intensity of the mutation probe with the mutation base A. The reference method will now be described as calling the unknown base in the sample sequence by using these intensities.

Figure 10A:
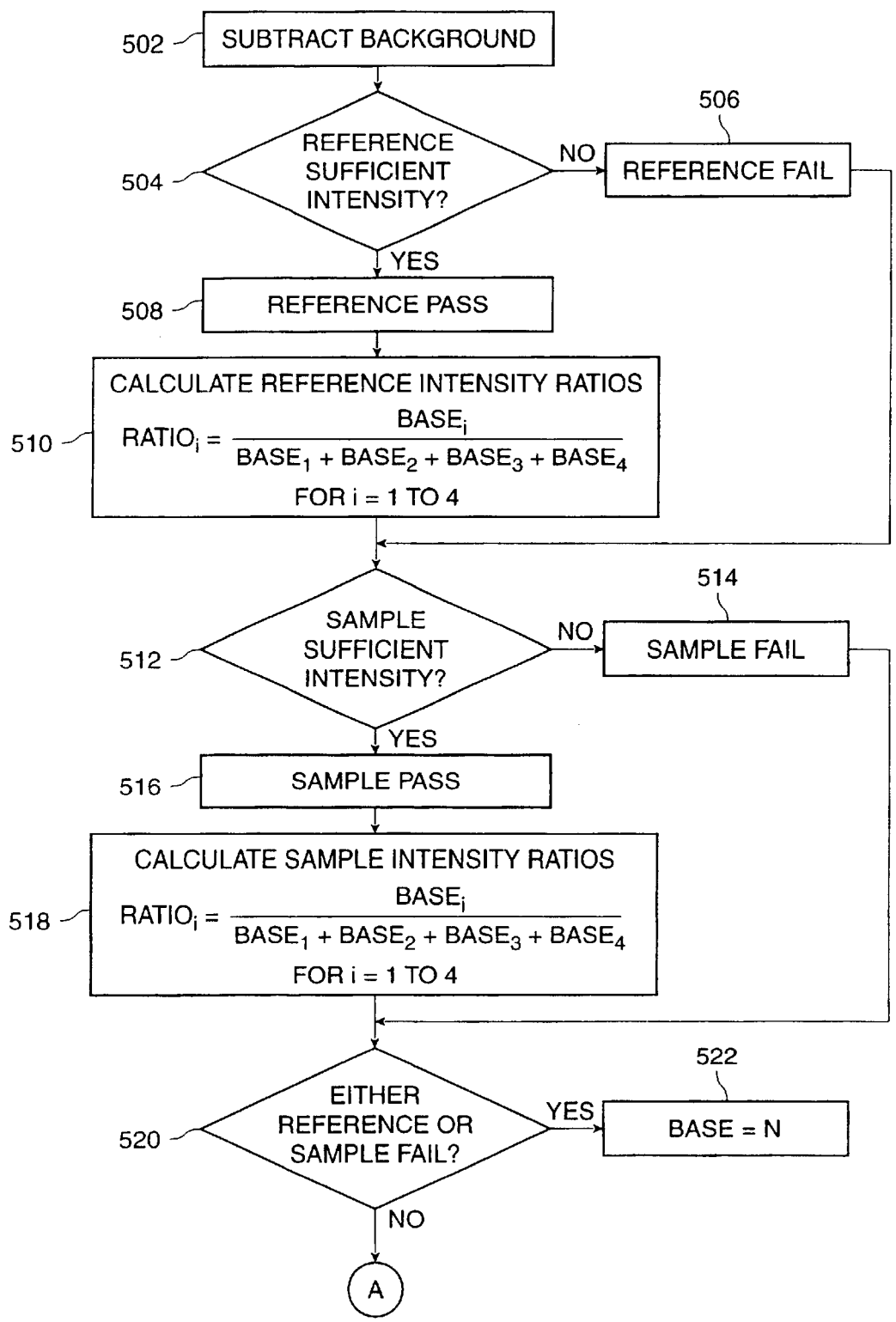
Figure 10A:
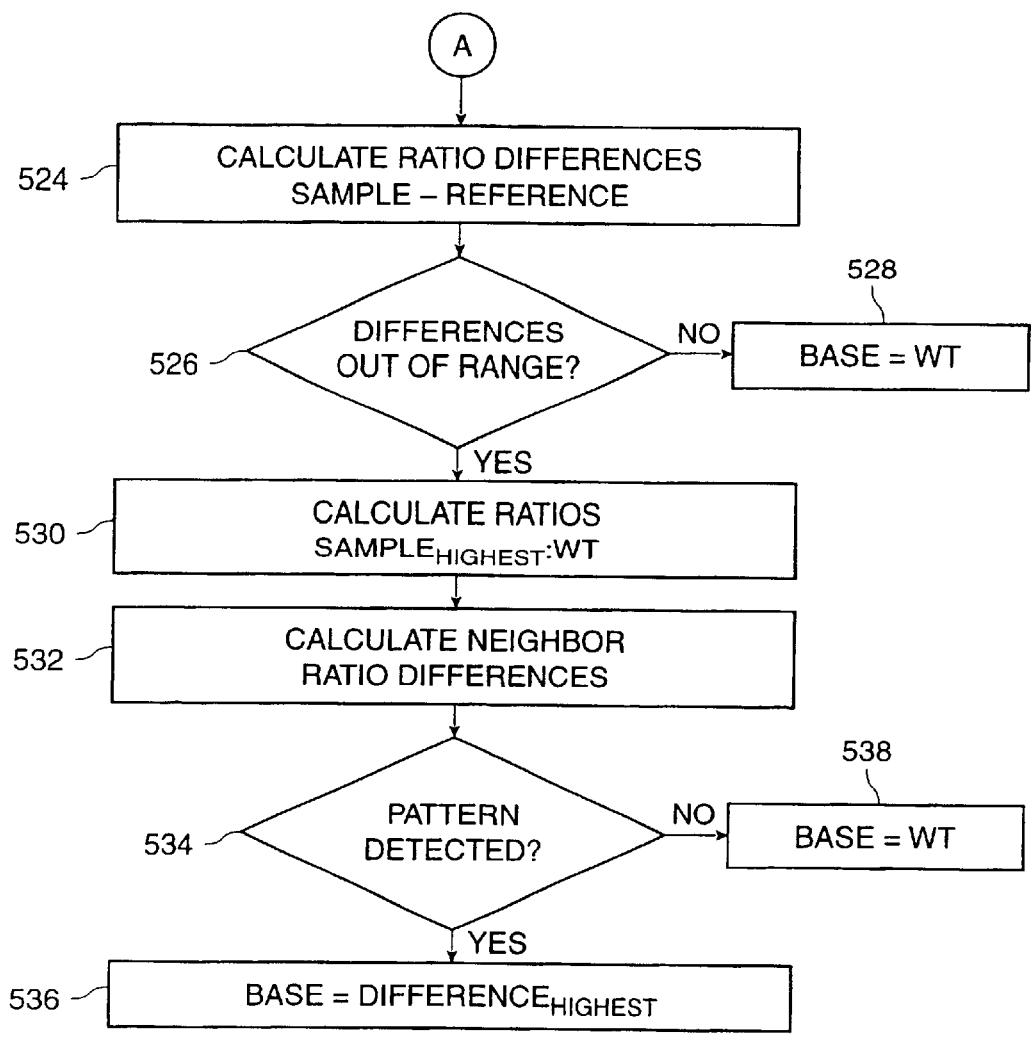

FIG. 10A illustrates the high level flow of one implementation of the reference method. For illustration purposes, the reference method is described as filling in the columns (identified by the numbers along the bottom) of the analysis table shown in FIG. 10B. However, the generation of an analysis table is not necessary to practice the method. The analysis table is shown to aid the reader in understanding the method.

At step 402 the four base intensities of the reference and sample sequences are adjusted by subtracting the background or "blank" cell intensity from each base intensity. Each set of "mutation" probes has an associated "blank" cell. Suppose that the reference "blank" cell intensity is 1 and the sample "blank" cell intensity is 2. The base intensities are then background subtracted as follows:

| Reference          | Sample            |
| ------------------ | ----------------- |
| A -> 12 – 1 = 11   | A -> 11 – 2 = 9   |
| C ->  9 – 1 =  8 | C -> 30 – 2 = 28  |
| G -> 80 – 1 = 79   | G -> 60 – 2 = 58  |
| T -> 15 – 1 = 14   | T ->  6 – 2 = 4 |

Preferably, if a base intensity is then less than or equal to zero, the base intensity is set equal to a small positive number to prevent division by zero or negative numbers in future calculations.

For identification, the position of each base of interest in the reference and sample sequences is placed in column 1 of the analysis table. Also, since the reference sequence is a known sequence, the base at this position is known and is referred to as the reference wild-type. The reference wild-type is placed in column 2 of the analysis table, which is C for this example.

At step 404 the base intensity associated with the reference wild-type (column 2 of the analysis table) is checked to see if it has sufficient intensity to call the unknown base. In this example, the reference wild-type is C. However, the base intensity associated with the wild-type is the G base intensity, which is 79 in this example. This is because the base intensities actually represent the complementary "mutation" probes. The G base intensity is checked by determining if its intensity is greater than a predetermined background difference cutoff. The background difference cutoff is a number that specifies the intensity the base intensities must be above the background intensity in order to correctly call the unknown base. Thus, the base intensity associated with the reference wild-type must be greater than the background difference cutoff or the unknown base is not callable.

If the background difference cutoff is 5, the base intensity associated with the reference wild-type has sufficient intensity (79>5) so a P (pass) is placed in column 3 of the analysis table as shown at step 406. Otherwise, at step 407 an F (fail) is placed in column 3 of the analysis table.

At step 408 the ratio of the base intensity associated with the reference wild-type to each of the possible bases are calculated. The ratio of the base intensity associated with the reference wild-type to itself will be 1 and the other ratios will usually be greater than 1. The base intensity associated with the reference wild-type is G so the following ratios are calculated:

G:A→79/11=7.2
G:C→79/8=9.9
G:G→79/79=1.0
G:T→79/14=5.6

These ratios are placed in columns 4 through 7 of the analysis table, respectively.

At step 410 the highest base intensity associated with the sample sequence is checked to see if it has sufficient intensity to call the unknown base. The highest base intensity is checked by determining if the intensity is greater than the background difference cutoff. Thus, the highest base intensity must be greater than the background difference cutoff or the unknown base is not callable.

Again, if the background difference cutoff is 5, the highest base intensity, which is G in this example, has sufficient intensity (58>5) so a P (pass) is placed in column 8 of the analysis table as shown at step 412. Otherwise, at step 413 an F (fail) is placed in column 8 of the analysis table.

At step 414 the ratios of the highest base intensity of the sample to each of the possible bases are calculated. The ratio of the highest base intensity to itself will be 1 and the other ratios will usually be greater than 1. Thus, the highest base intensity is G so the following ratios are calculated:

G:A→58/9=6.4
G:C→58/28=2.3
G:G→58/58=1.0
G:T→58/4=14.5

These ratios are placed in columns 9 through 12 of the analysis table, respectively.

At step 416 if both the reference and sample sequence probes failed to have sufficient intensity to call the unknown base, meaning there is an 'F' in columns 3 and 8 of the analysis table, the unknown base is assigned the code N (insufficient intensity) as shown at step 418. An 'N' is placed in column 17 of the analysis table. Additionally, a confidence code of 9 is placed in column 18 of the analysis table where the confidence codes have the following meanings:

| Code | Meaning |
| ---- | ------- |
| 0    | Probable reference wild-type |
| 1    | Probable mutation |
| 2    | Reference sufficient intensity, insufficient intensity in sample suggests possible mutation |
| 3    | Borderline differences, unknown base ambiguous |
| 4    | Sample sufficient intensity, insufficient intensity in reference to allow comparison |
| 5–8  | Currently unassigned |
| 9    | Insufficient intensity in reference and sample, no interpretation possible |

The confidence codes are useful for indicating to the user the resulting analysis of the reference method.

At step 420 if only the reference sequence probes failed to have sufficient intensity to call the unknown base, meaning there is an 'F' in column 3 and a 'P' in column 8 of the analysis table, the unknown base is assigned the code N (insufficient intensity) as shown at step 422. An 'N' is placed in column 17 and a confidence code of 4 is placed in column 18 of the analysis table.

At step 424 if only the sample sequence probes failed to have sufficient intensity to call the unknown base, meaning there is a 'P' in column 3 and a 'F' in column 8 of the analysis table, the unknown base is assigned the code N (insufficient intensity) as shown at step 426. An 'N' is placed in column 17 and a confidence code of 2 is placed in column 18 of the analysis table.

In this example, both the reference and sample sequence probes have sufficient intensity to call the unknown base. At step 428 the ratios of the reference ratios to the sample ratios for each base type are calculated. Thus, the ratio A:A (column 4 to column 9) is placed in column 13 of the analysis table. The ratio C:C (column 5 to column 10) is placed in column 14 of the analysis table. The ratio G:G (column 6 to column 11) is placed in column 15 of the analysis table. Lastly, the ratio T:T (column 7 to column 12) is placed in column 16 of the analysis table. These ratios are calculated as follows:

A:A→7.2/6.4=1.1
C:C→9.9/2.3=4.3
G:G→1.0/1.0=1.0
T:T→5.6/14.5=0.4

The unknown base is called by comparing these ratios of ratios to two predetermined values as follows.

At step 430 if all the ratios of ratios (columns 13 to 16 of the analysis table) are less than a predetermined lower ratio cutoff, the unknown base is assigned the code of the reference wild-type as shown at step 432. Thus, the code for the reference wild-type (as shown in column 2) would be placed in column 17 and a confidence code of 0 would be placed in column 18 of the analysis table.

At step 434 if all the ratios of ratios are less than a predetermined upper ratio cutoff, the unknown base is assigned an ambiguity code that indicates the unknown base may be any one of the bases that has a complementary ratio of ratios greater than the lower ratio cutoff and less than the upper ratio cutoff as shown at step 436. Thus, if the ratio of ratios for A:A, C:C and G:G are all greater than the lower ratio cutoff and less than the upper ratio cutoff, the unknown base would be assigned the code B (meaning "not A"). This is because the ratios of ratios are complementary to their respective base as follows:

A:A→T
C:C→G
G:G→C so the unknown base would be called as being either C, G, or T, which is identified by the IUPAC code B. This ambiguity code would be placed in column 17 and a confidence code of 3 would be placed in column 18 of the analysis table.

At step 438 at least one of the ratios of ratios is greater than the upper ratio cutoff and the unknown base is called as the base complementary to the highest ratio of ratios. The code for the base complementary to the highest ratio of ratios would be placed in column 17 and a confidence code of 1 would be placed in column 18 of the analysis table.

Assume for the purposes of this example that the lower ratio cutoff is 1.5 and the upper ratio cutoff is 3. Again, the ratios of ratios are as follows:

A:A→1.1
C:C→4.3
G:G→1.0
T:T→0.4

As all the ratios of ratios are not less than the upper ratio cutoff, the unknown base is called the base complementary to the highest ratio of ratios. The highest ratio of ratios is C:C, which has a complementary base G. Thus, the unknown base is called G which is placed in column 17 and a confidence code of 1 is placed in column 18 of the analysis table.

The example shows how the unknown base in the sample nucleic acid sequence was correctly called as base G. Although the complementary "mutation" probe associated with the base G (3'-GCCT) did not have the highest fluorescence intensity, the unknown base was called as base G because the associated "mutation" probe had the highest ratio increase over the other "mutation" probes.

Figure 11A:
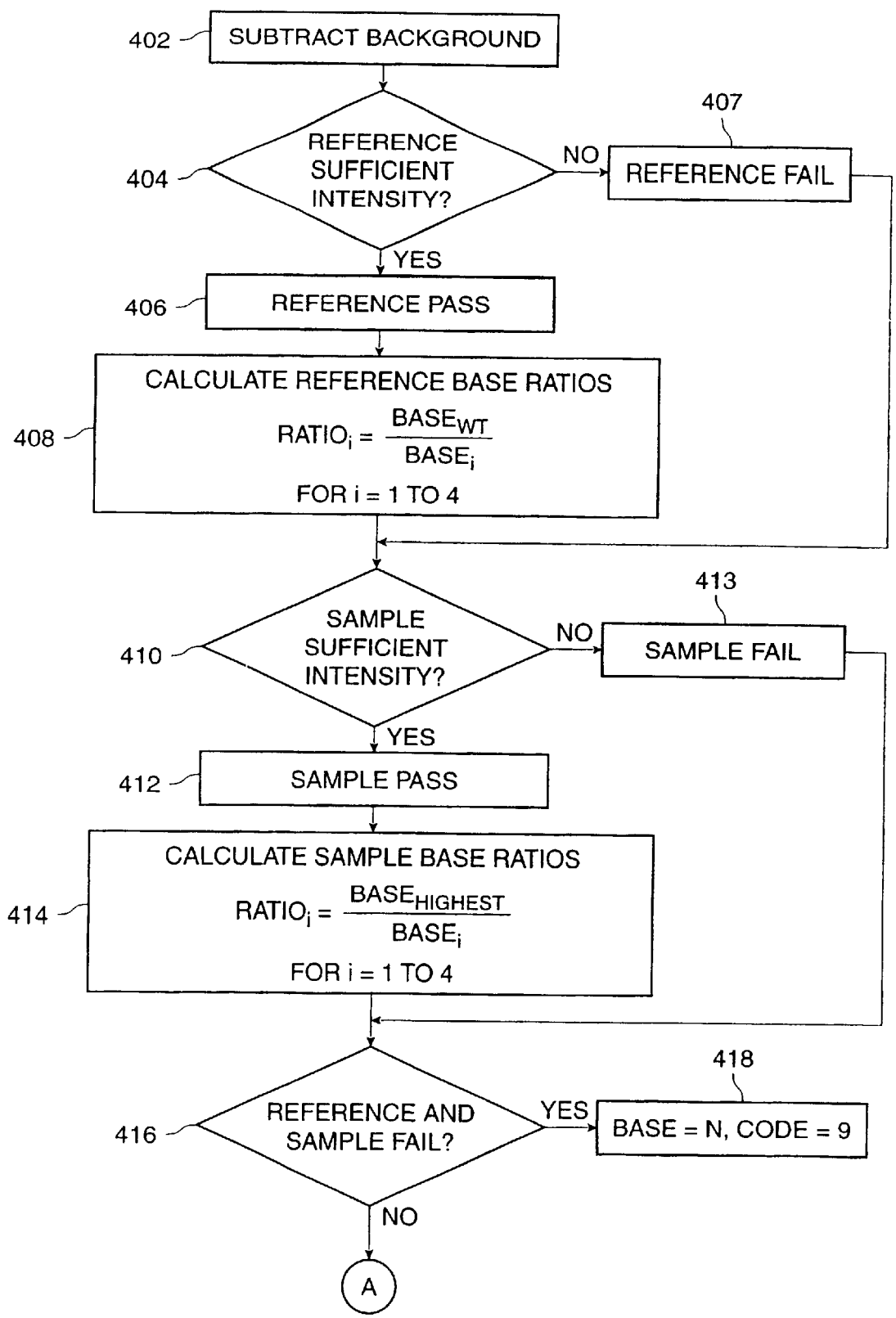
FIG. 11A illustrates the high level flow of another implementation of the reference method.
Figure 11A:
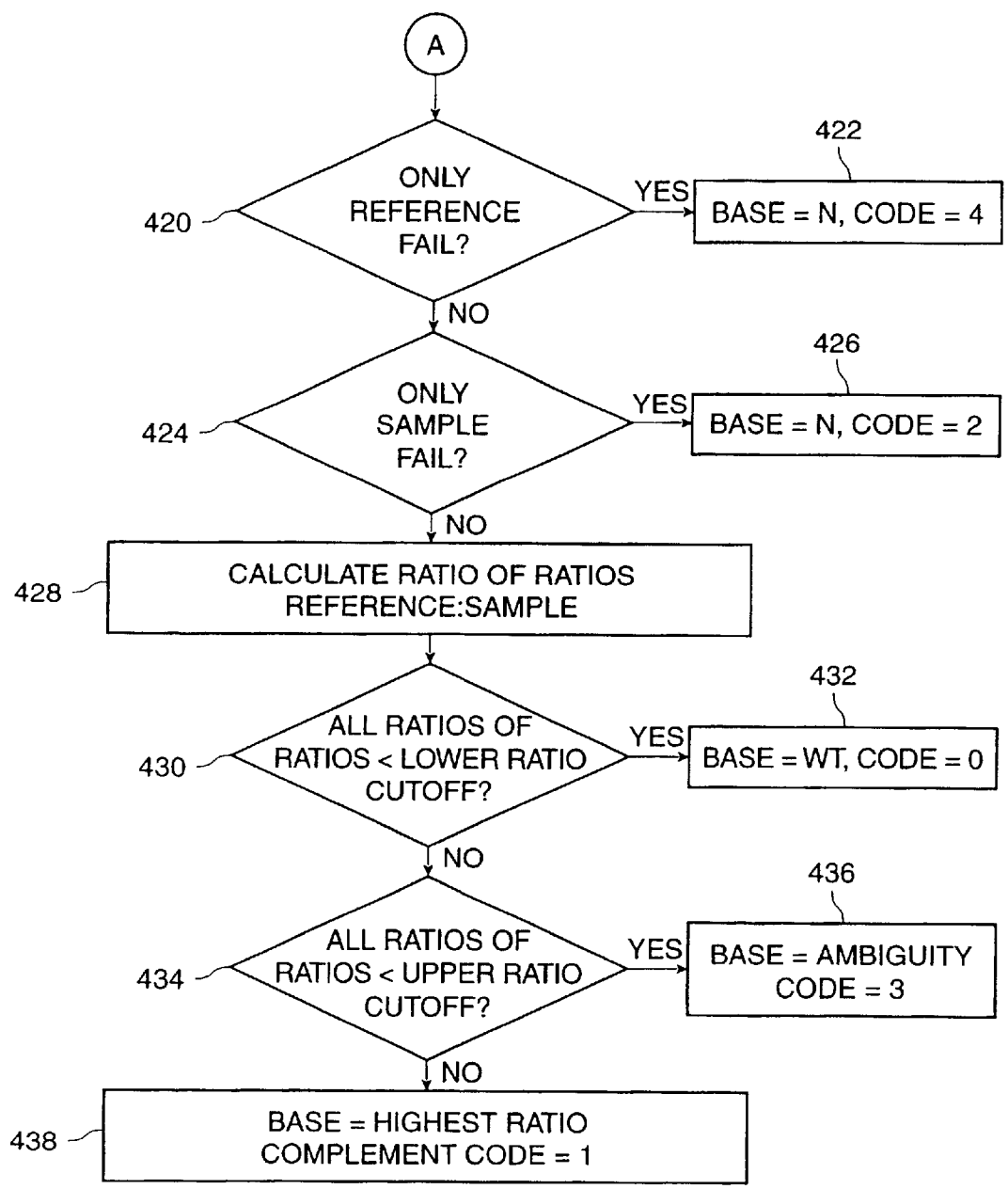

FIG. 11A illustrates the high level flow of another implementation of the reference method. As in the previous implementation, this implementation also compares the probe intensities of a reference sequence to the probe intensities of a sample sequence. However, this implementation differs conceptually from the previous implementation in that neighboring probe intensities are also analyzed, resulting in more accurate base calling.

As a simple example of this implementation of the reference method, suppose a reference sequence has a sequence of 5'-AAACCCAATCCACATCA-3' (SEQ ID NO:6) and a sample sequence has a sequence of 5'-AAACCCAGTCCACATCA-3' (SEQ ID NO:7), where the mutant base is underlined. Thus, there is a mutation of A to G. Suppose further that the reference and sample sequences are tiled on chips with the reference sequence being the chip wild-type. This implementation of the reference method will be described as identifying this mutation base.

For illustration purposes, this implementation of the reference method is described as filling in a data table shown in FIG. 11B (SEQ ID NO:6, SEQ ID NO:28, SEQ ID NO:29). Although the data table contains more data than is required for this implementation, the portions of the data table that are produced by steps in FIG. 11A are shown with the same reference numerals. The generation of a data table is not necessary, however, and is shown to aid the reader in understanding the method. The mutant base position is at position 241 in the reference and sample sequences, which is shown in bold in the data table.

At step 502 the base intensities of the reference and sample sequences are adjusted by subtracting the background or "blank" cell intensity from each base intensity. Preferably, if a base intensity is then less than or equal to zero, the base intensity is set equal to a small positive number to prevent division by zero or negative numbers. In the data table, data 502A is the background subtracted base intensities for the reference sequence and data 502B is the background subtracted base intensities for the sample sequence (also called the "mutant" sequence in the data table).

At step 504 the base intensity associated with the reference wild-type is checked to see if it has sufficient intensity to call the unknown base. In this example, the reference wild-type is base A at position 241. The base intensity associated with the reference wild-type is identified by a lower case "a" in the left hand column. Thus, the base intensities in the data table are not identified by their complements and the reference wild-type at the mutation position has an intensity of 385. The reference wild-type intensity of 385 is checked by determining if its intensity is greater than a predetermined background difference cutoff. The background difference cutoff is a number that specifies the intensity the base intensities must be over the background intensity in order to correctly call the unknown base. Thus, the base intensity associated with the reference wild-type must be greater than the background difference cutoff or the unknown base is not callable.

If the base intensity associated with the reference wild-type is not greater than the background difference cutoff, the wild-type sequence would fail to have sufficient intensity as shown at step 506. Otherwise, at step 508 the wild-type sequence would pass by having sufficient intensity.

At step 510 calculations are performed on the background subtracted base intensities of the reference sequence in order to "normalize" the intensities. Each position in the reference sequence has four background subtracted base intensities associated with it. The ratio of the intensity of each base to the sum of the intensities of the possible bases (all four) is calculated, resulting in four ratios, one for each base as shown in the data table. Thus, the following ratios would be calculated at each position in the reference sequence:

A ratio=A/(A+C=G=T)
C ratio=C/(A+C=G=T)
G ratio=G/(A+C=G=T)
T ratio=T/(A+C=G=T)

At position 241, A ratio would be the wild-type ratio. These ratios are generally calculated in order to "normalize" the intensity data as the photon counts may vary widely from experiment to experiment. Thus, the ratios provide a way of reconciling the intensity variations across experiments. Preferably, if the photon counts do not vary widely from experiment to experiment, the probe intensities do not need to be "normalized."

At step 512 the highest base intensity associated with the sample sequence is checked to see if it has sufficient intensity to call the unknown base. The intensity is checked by determining if the highest intensity sample base is greater than the background difference cutoff. If the intensity is not greater than the background difference cutoff, the sample sequence fails to have sufficient intensity as shown at step 514. Otherwise, at step 516 the sample sequence passes by having sufficient intensity.

At step 518 calculations are performed on the background subtracted base intensities of the sample sequence in order to "normalize" the intensities. Each position in the sample sequence has four background subtracted base intensities associated with it. The ratios of the intensity of each base to the sum of the intensities of the possible bases (all four) are calculated, resulting in four ratios, one for each base as shown in the data table.

At step 520 if either the reference or sample sequences failed to have sufficient intensity, the unknown base is assigned the code N (insufficient intensity) as shown at step 522.

At step 524 the normalized base intensities of the reference sequence are subtracted from the normalized base intensities of the sample sequence. Thus, at each position the following calculations are performed:

---

A Difference = Sample A Ratio − Reference A Ratio
C Difference = Sample C Ratio − Reference C Ratio
G Difference = Sample G Ratio − Reference G Ratio
T Difference = Sample T Ratio − Reference T Ratio

---

A Difference=Sample A Ratio−Reference A Ratio

C Difference=Sample C Ratio−Reference C Ratio

G Difference=Sample G Ratio−Reference G Ratio

T Difference=Sample T Ratio−Reference T Ratio where the reference and sample ratios are calculated at steps 510 and 518, respectively. The base differences resulting from these calculations are shown in the data table.

Figure 11C:
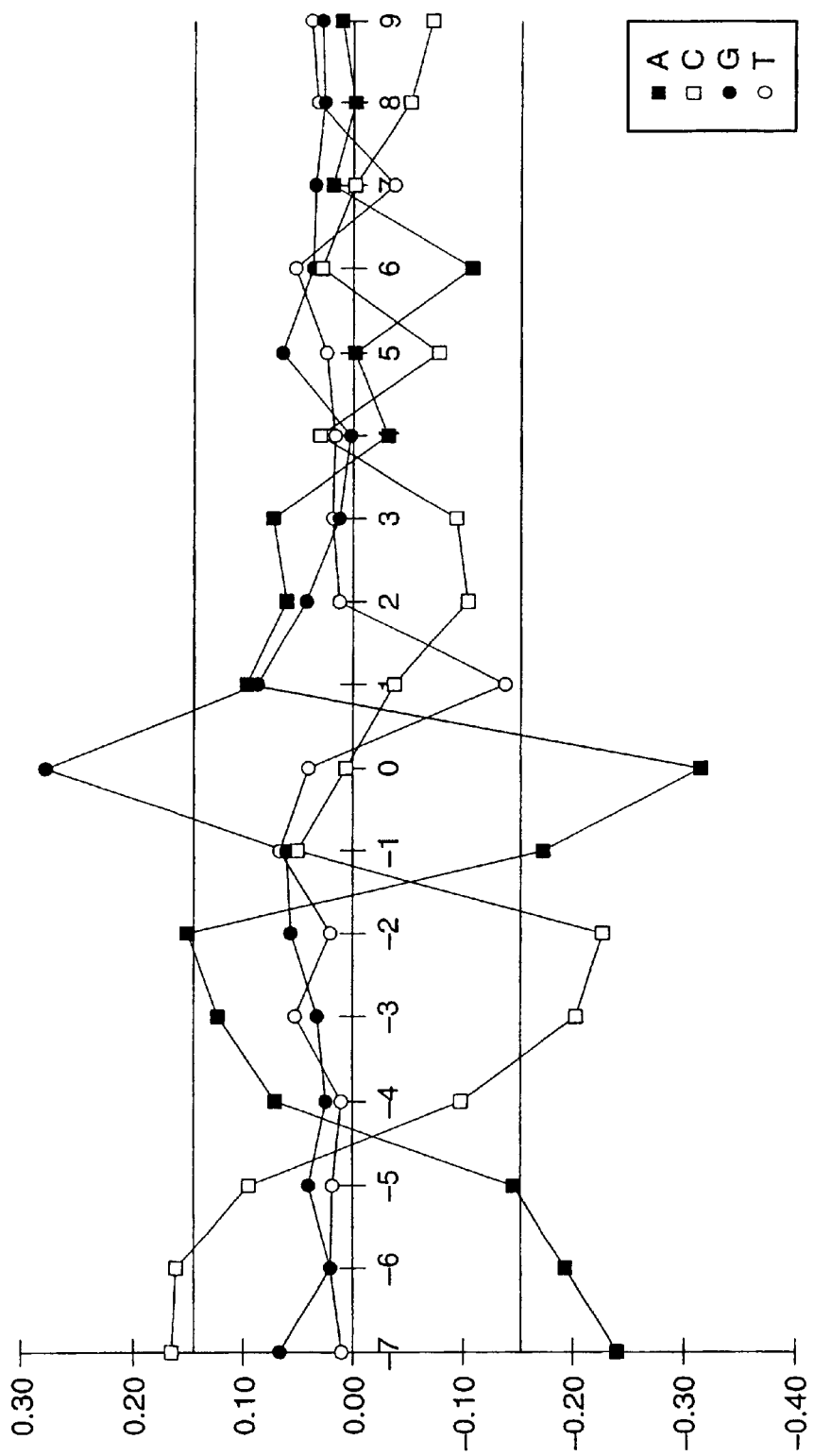
FIG. 11C shows a graph of the normalized sample base intensities minus the normalized reference base intensities.

At step 526 each position is checked to see if there is a base difference greater than an upper difference cutoff and a base difference lower than a lower difference cutoff. For example, FIG. 11C shows a graph the normalized sample base intensities minus the normalized reference base intensities. Suppose that the upper difference cutoff is 0.15 and the lower difference cutoff is −0.15 as shown by the horizontal lines in FIG. 11C. At the mutation position (labeled with a reference 0), the G difference is 0.28 which is greater than 0.15, the upper difference cutoff. Similarly, the A difference is −0.32 which is less than −0.15, the lower difference cutoff. As there is a base difference above the upper difference cutoff and a base difference below the lower difference cutoff, there may be mutation at this position.

If there is neither a base difference above the upper difference cutoff nor a base difference below the lower difference cutoff, the base at that position is assigned the code of the reference wild-type base as shown at step 528.

At step 530 the ratio of the highest background subtracted base intensity in the sample to the background subtracted reference wild-type base intensity is calculated. For example, at the mutation position 241 in the data table, the highest background subtracted base intensity in the sample is 571 (base G). The background subtracted reference wild-type base intensity is 385 (base A). The ratio of 571:385 is calculated and results in 1.48 as shown in the data table.

At step 532 these ratios are compared to a ratio at a neighboring position. The ratio for the $n^{th}$ position is subtracted from the ratio for the $r^{th}$ position, where r=n+1. For example, at the mutation position 241 in the data table, the ratio at position 242 (which equals 1.02) is subtracted from the ratio at position 241 (which equals 1.48). It has been found that a mutant can be confidently detected by analyzing the difference of these neighboring ratios.

Figure 11D:
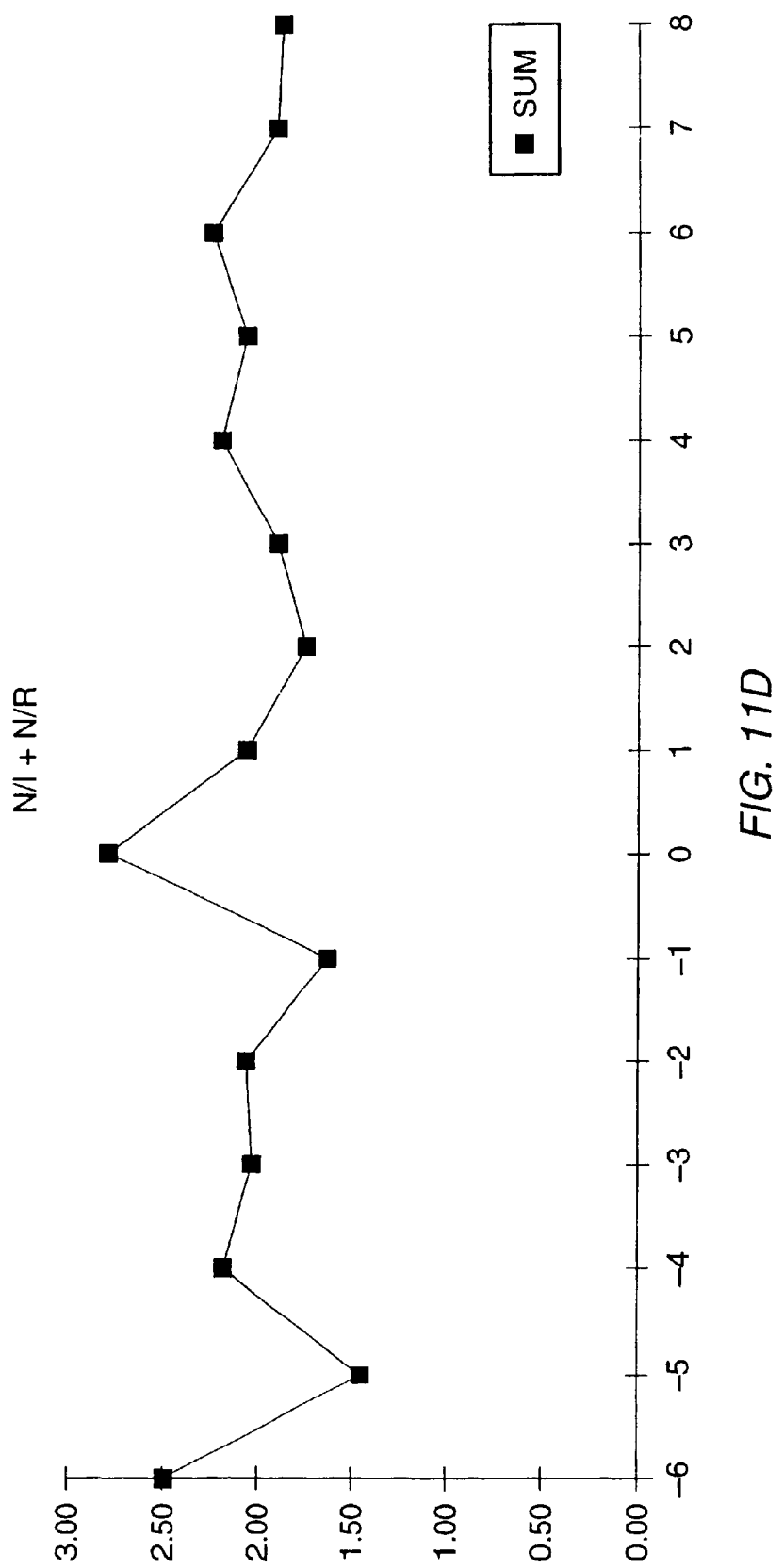
FIG. 11D shows other graphs of data in the data table.
Figure 11D:
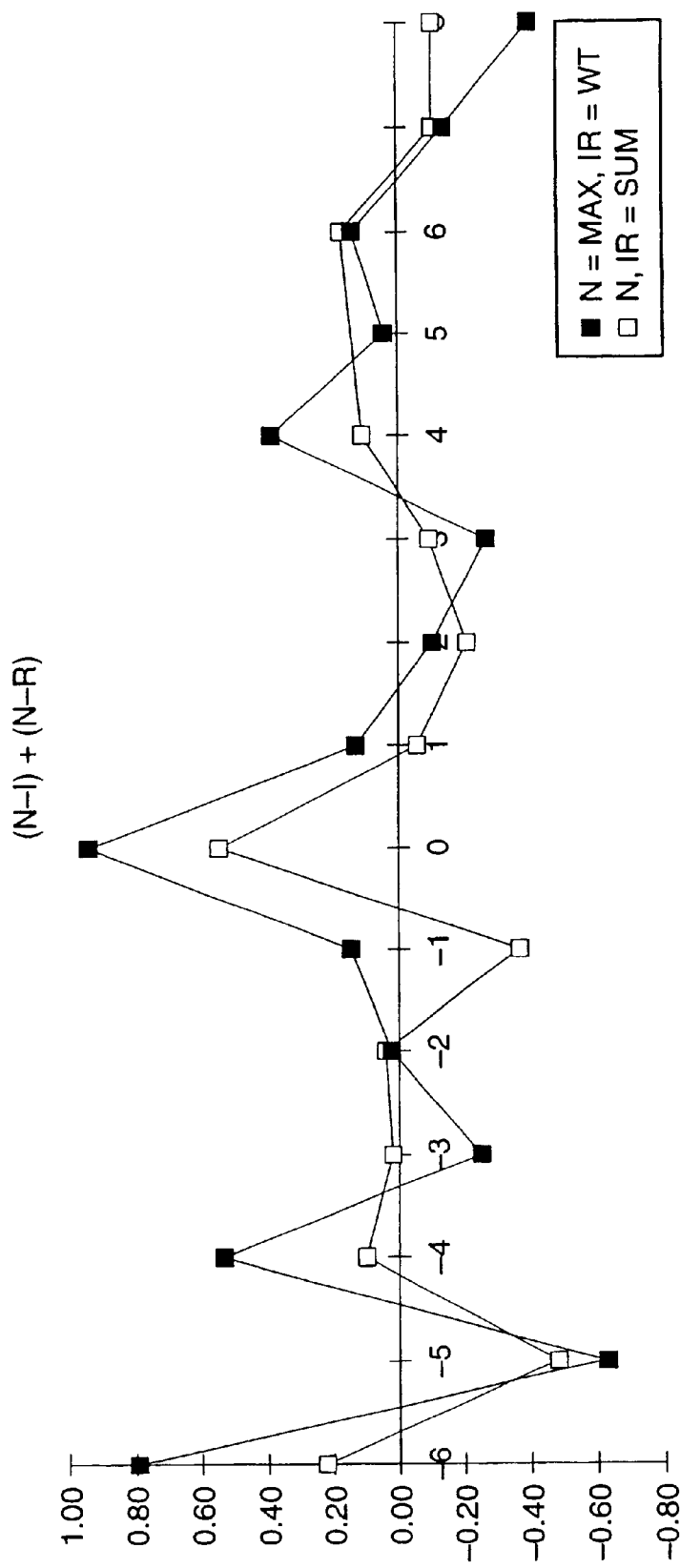
Figure 11D:
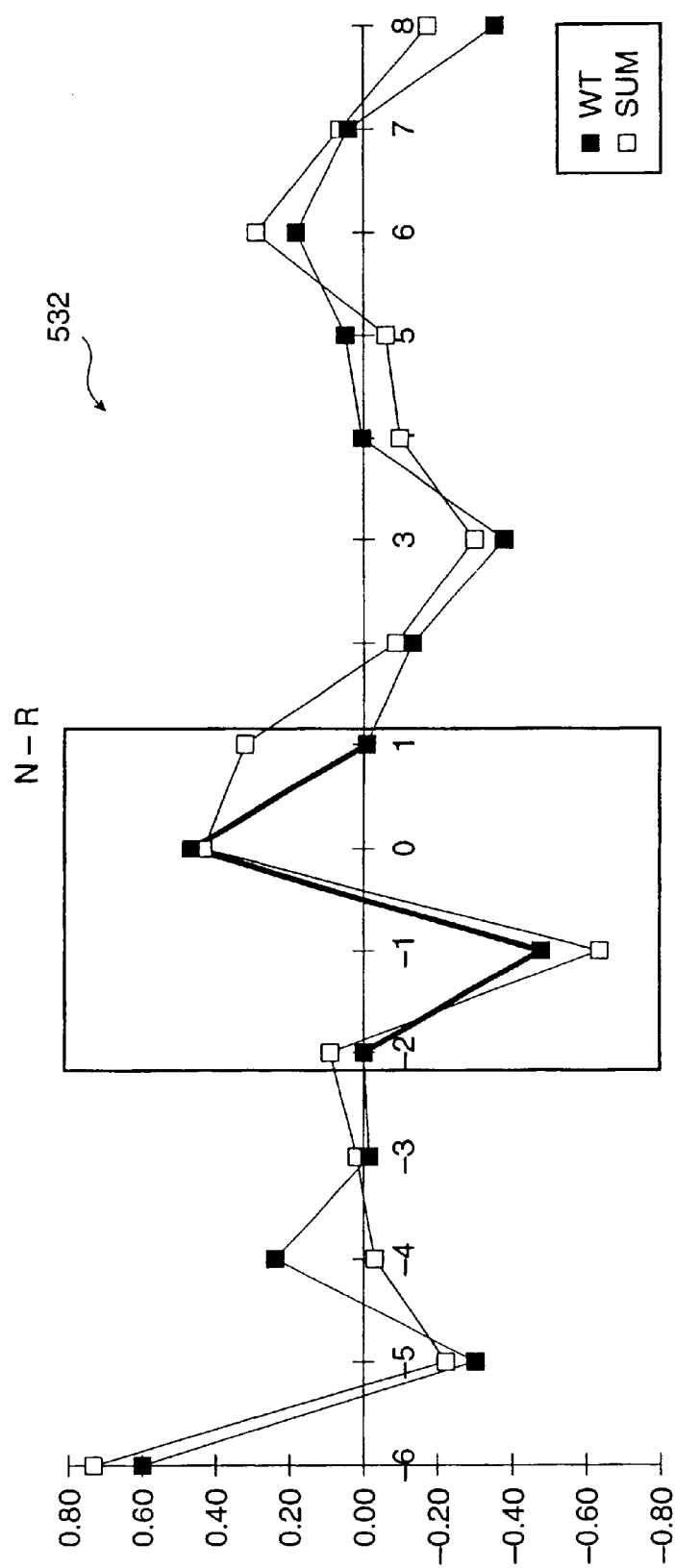
Figure 11D:
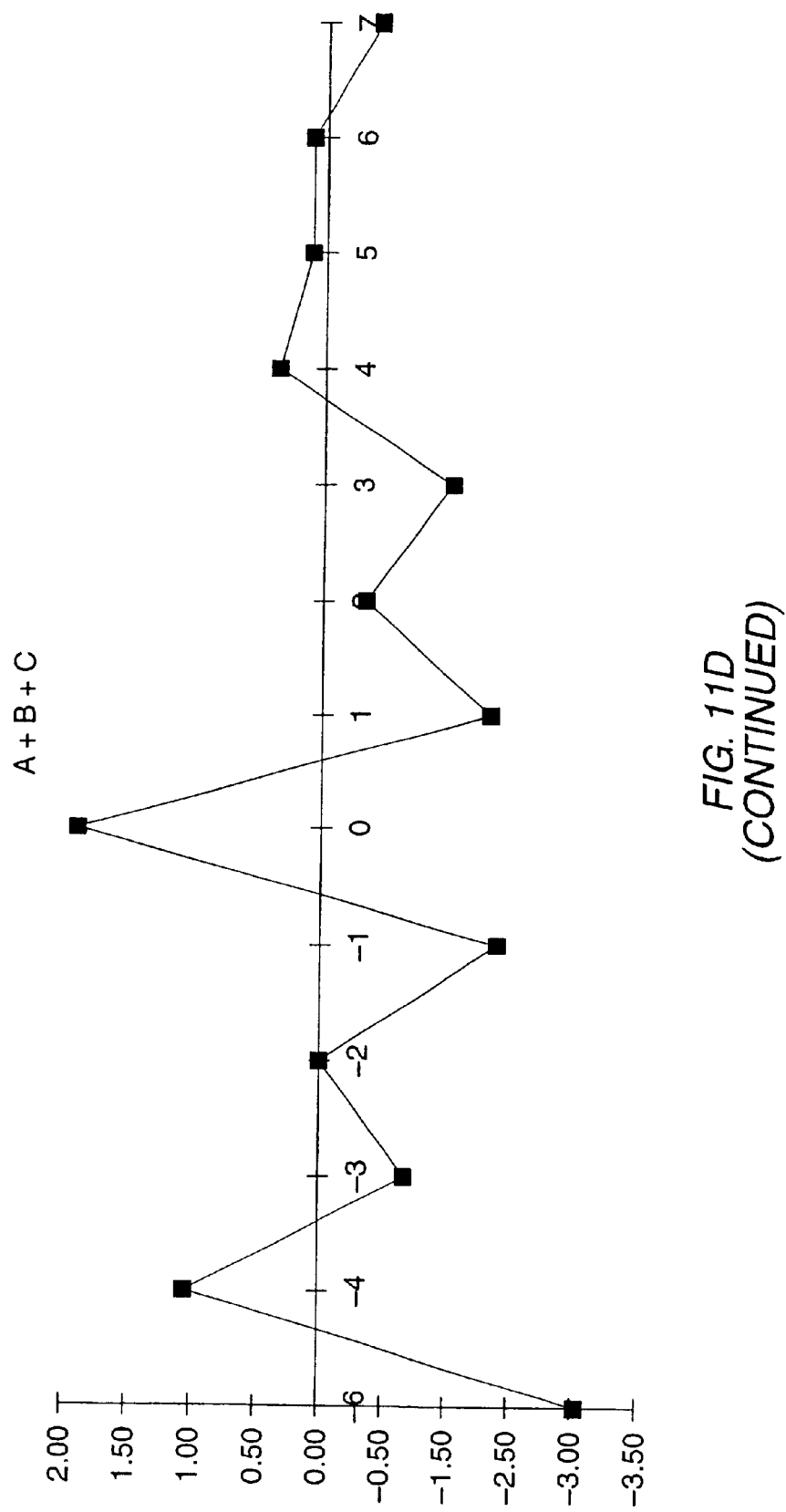

FIG. 11D shows other graphs of data in the data table. Of particular importance is the graph identified as 532 because this is a graph of the calculations at step 532. The pattern shown in a box in graph 532 has been found to be characteristic of a mutation. Thus, if this pattern is detected, the base is called as the base (or bases) with a normalized difference greater than the upper difference cutoff as shown at step 536. For example, the pattern was detected and at step 526 it was shown that base G had a normalized difference of 0.28, which is greater than the upper difference cutoff of 0.15. Therefore, the base at position 241 in the sample sequence is called a base G, which is a mutation from the reference sequence (A to G).

If the pattern is not detected at step 534, the base at that position is assigned the code of the reference wild-type base as shown at step 538.

This second implementation of the reference method is preferable in some instances as it takes into account probe intensities of neighboring probes. Thus, the first implementation may not have detected the A to G mutation in this example.

The advantage of the reference method is that the correct base can be called even in the presence of significant levels of cross-hybridization, as long as ratios of intensities are fairly consistent from experiment to experiment. In practice, the number of miscalls and ambiguities is significantly reduced, while the number of correct calls is actually increased, making the reference method very useful for identifying candidate mutations. The reference method has also been used to compare the reproducibility of experiments in terms of base calling.

IV. Statistical Method

The statistical method is a method of calling bases in a sample nucleic acid sequence. The statistical method utilizes the statistical variation across experiments to call the bases. Therefore, the statistical method is preferable when data from multiple experiments is available and the data is fairly consistent across the experiments. The method compares the probe intensities of a sample sequence to statistics of probe intensities of a reference sequence in multiple experiments.

For simplicity, the statistical method will be described as being used to identify one unknown base in a sample nucleic acid sequence. In practice, the method is used to identify many or all the bases in a nucleic acid sequence.

The unknown base will be called by comparing the probe intensities of a sample sequence to statistics on probe intensities of a reference sequence in multiple experiments. Generally, the probe intensities of the sample sequence and the reference sequence experiments are from chips having the same chip wild-type. However, the reference sequence may or may not be equal to the chip wild-type, as it may have mutations.

A base at the same position in the reference and sample sequences will be associated with up to four mutation probes and a "blank" cell. As before, because each mutation probe is identifiable by the mutation base, the mutation probes' intensities will be referred to as the "base intensities" of their respective mutation bases.

As a simple example of the statistical method, suppose a gene of interest (target) has the sequence 5'-AAAACTGAAAA-3' (SEQ ID NO:4). Suppose a reference sequence has the sequence 5'-AAAACCGAAAA-3' (SEQ ID NO:5), which differs from the target sequence by the underlined base. Suppose further that a sample sequence is suspected to have the same sequence as the target sequence except for a T base mutation at the underlined base position in 5'-AAAACTGAAAA-3' (SEQ ID NO:4). Suppose that in multiple experiments the reference sequence is marked and exposed to probes on a chip. Suppose further the sample sequence is also marked and exposed to probes on a chip.

The following are complementary "mutation" probes that could be used for a reference experiment and the sample sequence:

| Reference | Sample |
|---|---|
| 3'-TGAC | 3'-GACT |
| 3'-TGCC | 3'-GCCT |
| 3'-TGGC | 3'-GGCT |
| 3'-TGTC | 3'-GTCT |

The "mutation" probes shown for the reference sequence may be from only one experiment, the other experiments may have different "mutation" probes, chip wild-types, tiling methods, and the like. Although each fluorescence intensity is from a probe, since the probes may be identified by their unique mutation bases, the probe intensities may be identified by their respective bases as follows:

| Reference | Sample |
|---|---|
| 3'-TGAC -> A | 3'-GACT -> A |
| 3'-TGCC -> C | 3'-GCCT -> C |
| 3'-TGGC -> G | 3'-GGCT -> G |
| 3'-TGTC -> T | 3'-GTCT -> T |

Thus, base A of the reference sequence will be described as having an intensity which corresponds to the intensity of the mutation probe with the mutation base A. The statistical method will now be described as calling the unknown base in the sample sequence by using this example.

Figure 12:
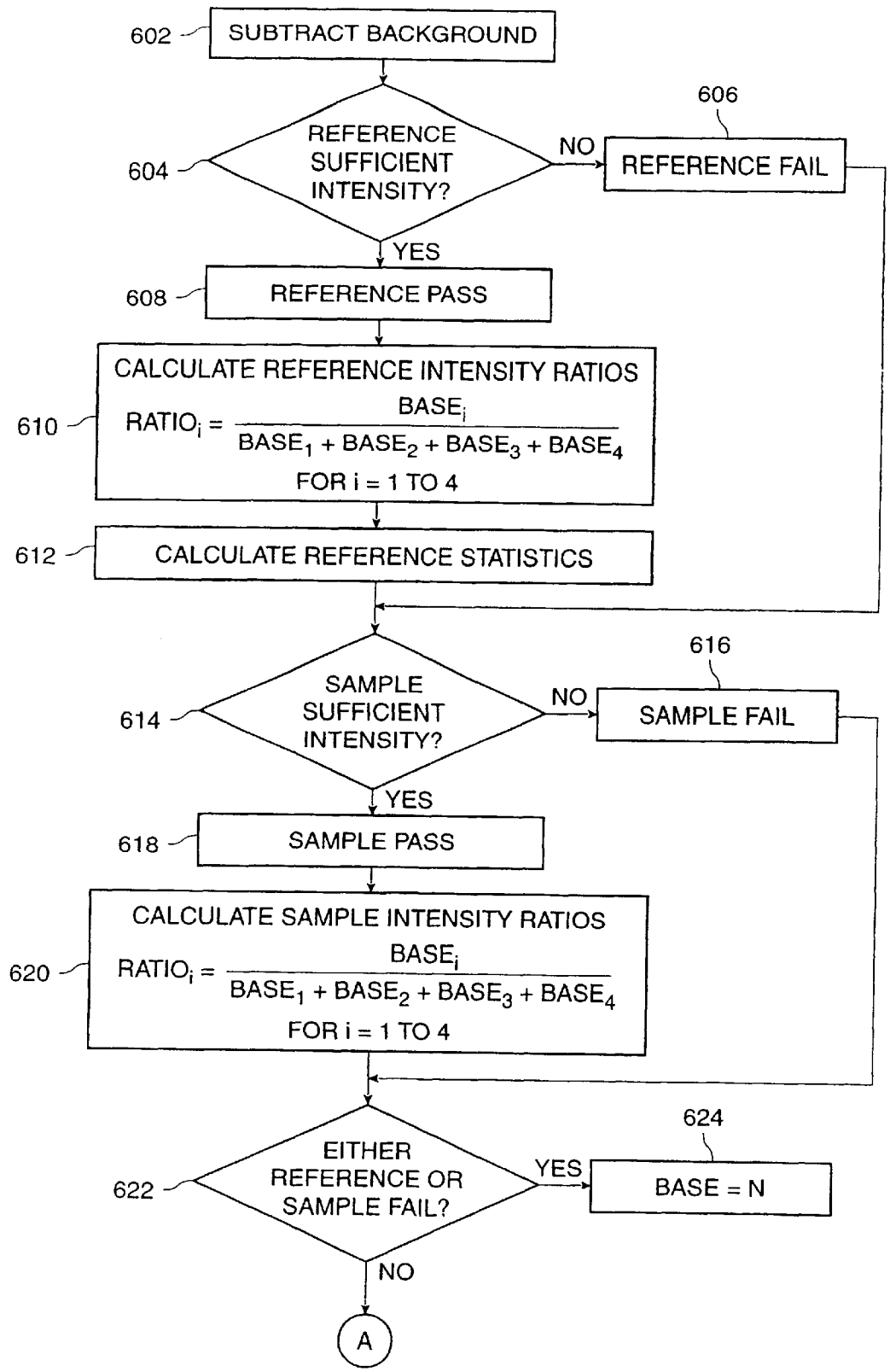
FIG. 12 illustrates the high level flow of the statistical method.
Figure 12:
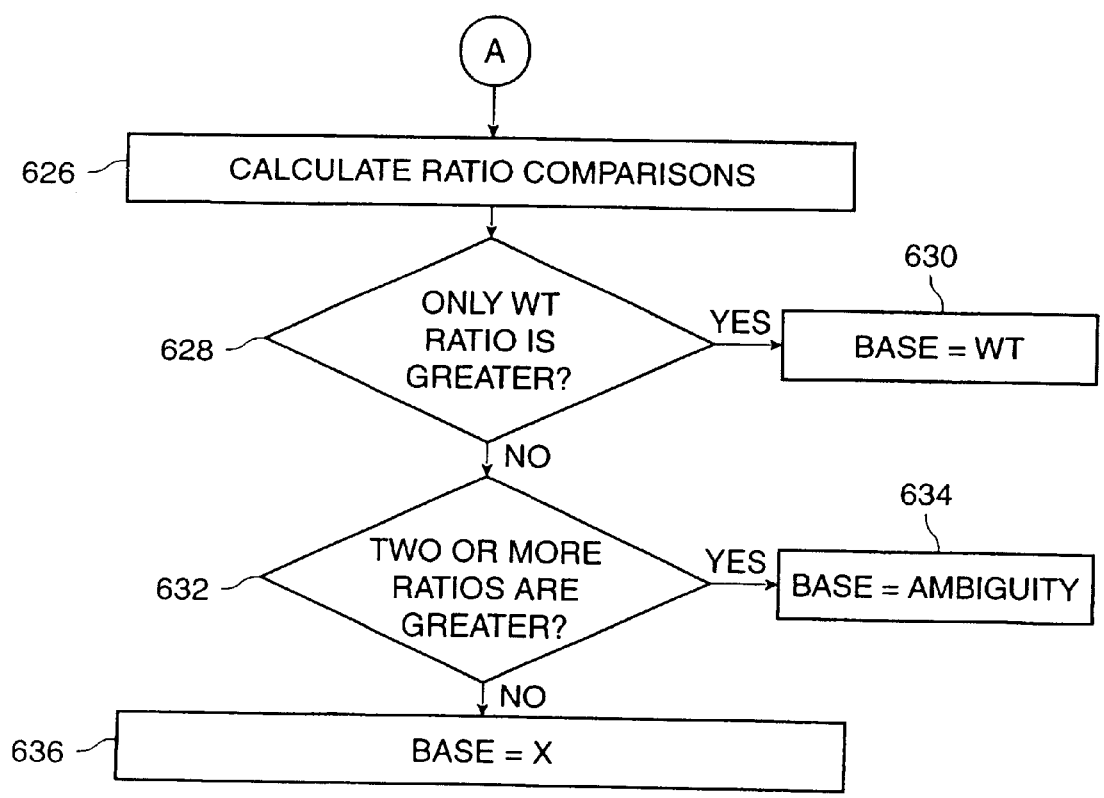

FIG. 12 illustrates the high level flow of the statistical method. At step 602 the four base intensities associated with the sample sequence and each of the multiple reference experiments are adjusted by subtracting the background or "blank" cell intensity from each base intensity. Preferably, if a base intensity is then less than or equal to zero, the base intensity is set equal to a small positive number to prevent division by zero or negative numbers.

At step 604 the intensities of the reference wild-type bases in the multiple experiments are checked to see if they all have sufficient intensity to call the unknown base. The intensities are checked by determining if the intensity of the reference wild-type base of an experiment is greater than a predetermined background difference cutoff. The wild-type probe shown earlier for the reference sequence is 3'-TGGC, and thus the G base intensity is the wild-type base intensity. These steps are analogous to steps in the other two methods described herein.

If the intensity of any one of the reference wild-type bases is not greater than the background difference cutoff, the wild-type experiments fail to have sufficient intensity as shown at step 606. Otherwise, at step 608 the wild-type experiments pass by having sufficient intensity.

At step 610 calculations are performed on the background subtracted base intensities of each of the reference experiments in order to "normalize" the intensities. Each reference experiment has four background subtracted base intensities associated with it: one wild-type and three for the other possible bases. In this example, the G base intensity is the wild-type, the A, C, and T base intensities being the "other" intensities. The ratios of the intensity of each base to the sum of the intensities of the possible bases (all four) are calculated, giving one wild-type ratio and three "other" ratios. Thus, the following ratios would be calculated:

A ratio=A/(A+C=G=T)

C ratio=C/(A+C=G=T)

G ratio=G/(A+C=G=T)

T ratio=T/(A+C=G=T)

where G ratio is the wild-type ratio and A, C, and T ratios are the "other" ratios. These four ratios are calculated for each reference experiment. Thus if the number of reference experiments is n, there would be 4n ratios calculated. These ratios are generally calculated in order to "normalize" the intensity data, as the photon counts may vary widely from experiment to experiment. However, if the probe intensities do not vary widely from experiment to experiment, the probe intensities do not need to be "normalized."

At step 612 statistics are prepared for the ratios calculated for each of the reference experiments. As stated before, each reference experiment will be associated with one wild-type ratio and three "other" ratios. The mean and standard deviation are calculated for all the wild-type ratios. The mean and standard deviation are also calculated for each of the other ratios, resulting in three other means and standard deviations for each of the bases that is not the wild-type base. Therefore, the following would be calculated:

Mean and standard deviation of A ratios

Mean and standard deviation of C ratios

Mean and standard deviation of G ratios

Mean and standard deviation of T ratios where the mean and standard deviation of the G ratios are also known as the wild-type mean and the wild-type standard deviation, respectively. The mean and standard deviation of the A, C, and T means and standard deviations are also known collectively as the "other" means and standard deviations.

Suppose that the preceding calculations produced the following data:

A ratios→mean=0.16 std. dev.=0.003

C ratios→mean=0.03 std. dev.=0.002

G ratios→mean=0.71 std. dev.=0.050

T ratios→mean=0.11 std. dev.=0.004

In one embodiment, the steps up to and including step 612 are performed in a preprocessing stage for the multiple wild-type experiments. The results of the preprocessing stage are stored in a file so that the reference calculations do not have to be repeatedly calculated, improving performance. Microfiche Appendices C and D contain the programming code to perform the preprocessing stage.

At step 614 the highest base intensity associated with the sample sequence is checked to see if it has sufficient intensity to call the unknown base. The intensity is checked by determining if the highest intensity unknown base is greater than the background difference cutoff. If the intensity is not greater than the background difference cutoff, the sample sequence fails to have sufficient intensity as shown at step 616. Otherwise, at step 618 the sample sequence passes by having sufficient intensity.

At step 620 calculations are performed on the four background subtracted intensities of the sample sequence. The ratios of the background subtracted intensity of each base to the sum of the background subtracted intensities of the possible bases (all four) are calculated, giving four ratios, one for each base. For consistency, the ratio associated with the reference wild-type base is called the wild-type ratio, with there being three "other" ratios. Thus, the following ratios are calculated:

A ratio=A/(A+C+G+T)

C ratio=C/(A+C+G+T)

G ratio=G/(A+C+G+T)

T ratio=T/(A+C+G+T)

where ratio G is the wild-type ratio and ratios A, C, and T are the "other" ratios.

Suppose the background subtracted intensities associated with the sample are as follows:

A→310

C→50

G→26

T→100

Then, the corresponding ratios would be as follows:

A ratio=310/(310+50+26+100)=0.64

C ratio=50/(310+50+26+100)=0.10

G ratio=26/(310+50+26+100)=0.05

T ratio=100/(310+50 +26+100)=0.21

At step 622 if either the reference experiments or the sample sequence failed to have sufficient intensity, the unknown base is assigned the code N (insufficient intensity) as shown at step 624.

At step 626 the wild-type and "other" ratios associated with the sample sequence are compared to statistical expressions. The statistical expressions include four predetermined standard deviation cutoffs, one associated with each base. Thus, there is a standard deviation cutoff for each of the bases A, C, G, and T. The localized standard deviation cutoffs allow the unknown base to be called with higher precision because each standard deviation cutoff can be set to a different value. Suppose the standard deviation cutoffs are set as follows:

A standard deviation cutoff→4

C standard deviation cutoff→2

G standard deviation cutoff→8

T standard deviation cutoff→4

The wild-type base ratio associated with the sample is compared to a corresponding statistical expression:

WT ratio≧WT mean−(WT std. dev.*WT base std. dev. cutoff)

where the WT base std. dev. cutoff is the standard deviation cutoff for the wild-type base. As the wild-type base is G, the above comparison solves to the following:

0.05≧0.71−(0.050*8)

0.05≧0.31 which is not a true expression (0.05 is not greater than 0.31).

Each of the "other" ratios associated with the sample is compared to a corresponding statistical expression:

Other ratio>Other mean+(Other std. dev.*Other base std. dev. cutoff)

where the Other base std. dev. cutoff is the standard deviation cutoff for the particular "other" base. Thus, the above comparison solves to the following three expressions:

A→0.64>0.16+(0.003*4) 0.64>0.17

C→0.10>0.03+(0.002*2) 0.10>0.03

T→0.21>0.11+(0.004*4) 0.21>0.13 which are all true expressions.

At step 628 if only the wild-type ratio of the sample sequence was greater than the statistical expression, the unknown base is assigned the code of the reference wild-type base as shown at step 630.

At step 632 if one or more of the "other" ratios of the sample sequence were greater than their respective statistical expressions, the unknown base is assigned an ambiguity code that indicates the unknown base may be any one of the complements of these bases, including the reference wild-type. In this example, the "other" ratios for A, C, and T were all greater than their corresponding statistical expression. Thus, the unknown base would be called the complements of these bases, represented by the subset T, G, and A. Thus, the unknown base would be assigned the code D (meaning "not C").

If none of the ratios are greater than their respective statistical expressions, the unknown base is assigned the code X (insufficient discrimination) as shown at step 636.

The statistical method provides accurate base calling because it utilizes statistical data from multiple reference experiments to call the unknown base. The statistical method has also been used to implement confidence estimates and calling of mixed sequences.

V. Pooling Processing

The present invention provides pooling processing which is a method of processing reference and sample nucleic acid sequences together to reduce variations across individual experiments. In the representative embodiment discussed herein, the reference and sample nucleic acid sequences are labeled with different fluorescent markers emitting light at different wavelengths. However, the nucleic acids may be labeled with other types of markers including distinguishable radioactive markers.

After the reference and sample nucleic acid sequences are labeled with different color fluorescent markers, the labeled reference and sample nucleic acid sequences are then combined and processed together. An apparatus for detecting targets labeled with different markers is provided in U.S. application Ser. No. 08/195,889 and is hereby incorporated by reference for all purposes.

Figure 13:
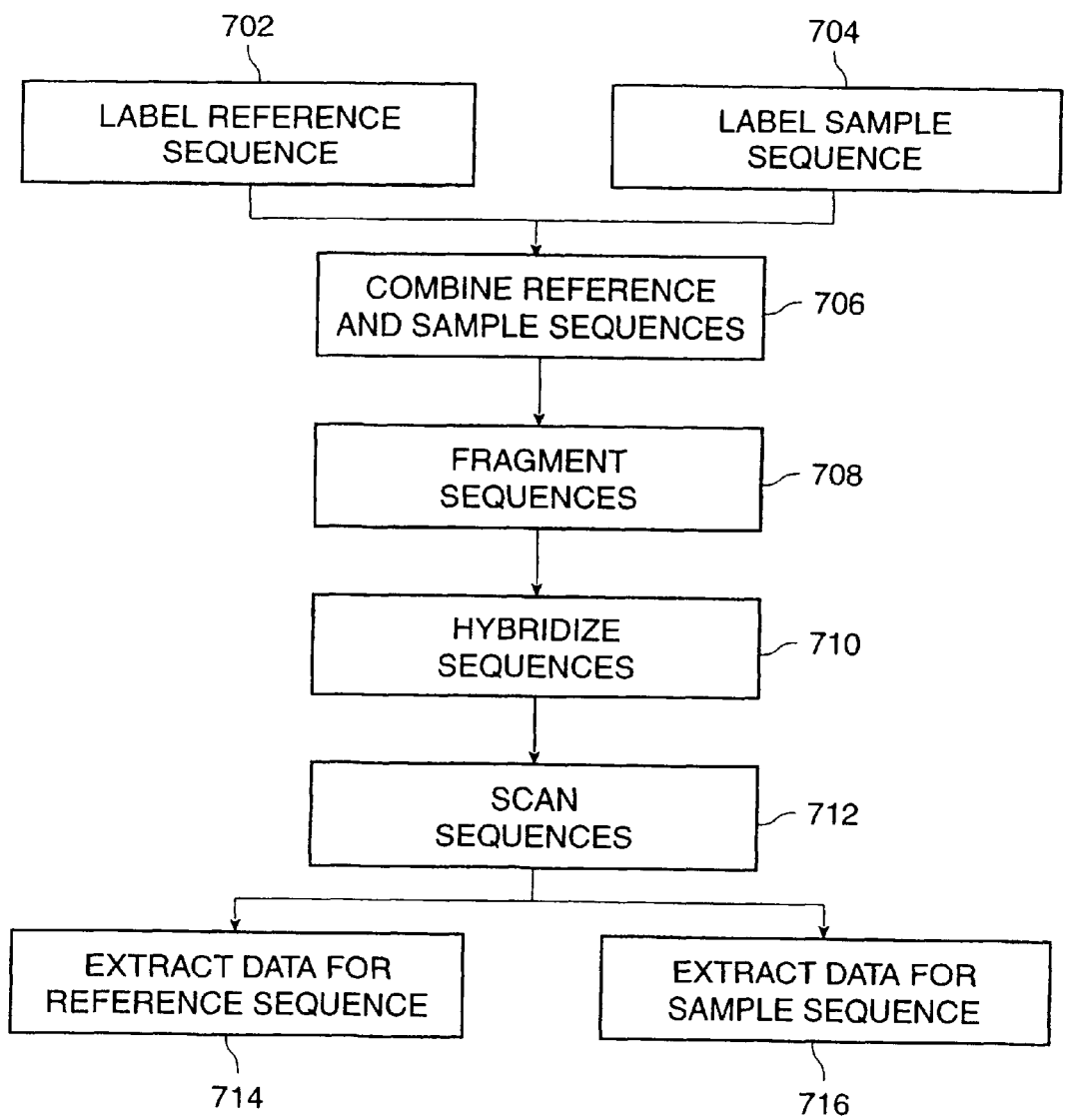
FIG. 13 illustrates the pooling processing of a reference and sample nucleic acid sequence.

FIG. 13 illustrates the pooling processing of a reference and sample nucleic acid sequence. At step 702 a reference nucleic acid sequence is marked with a fluorescent dye, such as fluorescein. At step 704 a sample nucleic acid sequence is marked with a dye that, upon excitation, emits light of a different wavelength than that of the fluorescent dye of the reference sequence. For example, the sample nucleic acid sequence may be marked with rhodamine. Alternatively, the sample nucleic acid sequence may be marked by attaching biotin to the sample sequence which will subsequently bind to streptavidin labeled with phycoerythrin. Of course, either sequence may be marked with these or other dyes or other kinds of markers (e.g., radioactive) as long as the other sequence is marked with a marker that is distinguishable.

At step 706 the labeled reference sequence and the labeled sample sequence are combined. After this step, processing continues in the same manner as for only one labeled sequence. At step 708 the sequences are fragmented. The fragmented nucleic acid sequences are then hybridized on a chip containing probes as shown at step 710.

At step 712 a scanner generates image files that indicate the locations where the labeled nucleic acids bound to the chip. There is typically some overlap between the two signals. This is corrected for prior to further analysis, i.e., after correction, the data files correspond to "reference" and "sample." In general, the scanner generates an image file by focusing excitation light on the hybridized chip and detecting the fluorescent light that is emitted. The marker emitting the fluorescent light can be identified by the wavelength of the light. For example, the fluorescence peak of fluorescein is about 530 nm while that of a typical rhodamine dye is about 580 nm.

The scanner creates an image file for the data associated with each fluorescent marker, indicating the locations where the correspondingly labeled nucleic acid bound to the chip. Based upon an analysis of the fluorescence intensities and locations, it becomes possible to extract information such as the monomer sequence of DNA or RNA.

Pooling processing reduces variations across individual experiments because much of the test environment is common. Although pooling processing has been described as being used to improve the combined processing of reference and sample nucleic acid sequences, the process may also be used for two reference sequences, two sample sequences, or multiple sequences by utilizing multiple distinguishable markers.

Pooling processing may also be utilized with methods of the present invention of identifying mutations in a sample nucleic acid sequence. These methods are highly accurate in identifying single mutations, locating multiple mutations and removing false positives for mutations, where a false positive is a base that has erroneously been identified as a mutation. These methods utilize hybridization data from more than one base position to identify the likely position of mutations. The interrogation position on the probes is utilized to more accurately identify likely mutations which makes more efficient use of base calling methods. These methods may be advantageously combined with the base calling methods described herein to efficiently and accurately sequence a sample nucleic acid sequence.

As discussed earlier in reference to FIG. 8, the fluorescent intensities of cells near an interrogation position having a mutation are relatively dark which creates "dark regions" around the mutation. These lower fluorescent intensities result because the cells at interrogation positions near a mutation do not contain probes that are perfectly complementary to the sample sequence. Thus, the hybridization of these probes with the sample sequence is lower. The characteristics of these "dark regions" may be utilized to identify mutations and false positives.

For example, a sample sequence and a reference sequence were labeled with different fluorescent markers, in this case fluorescein and biotin/phycoerythrin. The sample and reference sequences are known and the sample sequence is identical to the reference sequence except for mutations at certain known positions. The sample and reference sequences were then processing together using the pooling processing described above and the sequences were hybridized to a chip including wild-type probes that are perfectly complementary to the reference sequence. The chip included 20-mer probes with the interrogation position of each probe being at the $12^{th}$ base position in the probe.

Figure 14A:
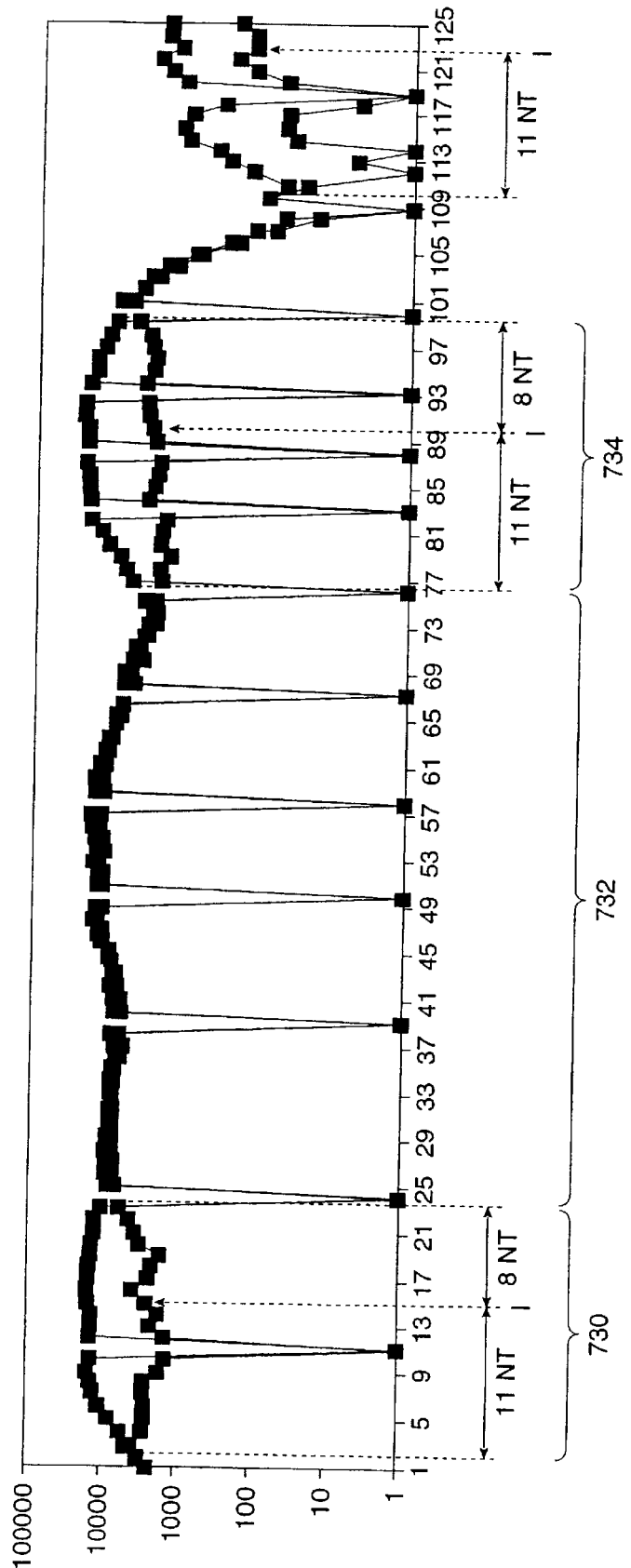
FIGS. 14A and 14C show graphs of scaled fluorescent intensities of wild-type probes hybridizing with sample and reference sequences and 14B shows a hypothetical graph of fluorescent intensities of wild-type probes hybridizing with two sample sequences and a reference sequence.

FIG. 14A shows a graph of the scaled fluorescent intensities (photon counts) of the wild-type probes hybridizing with the sample and reference sequences. Along the bottom of the graph are numbers which represent wild-type cell positions on the chip. The photon counts of the probes in the wild-type cells are plotted on a logarithmic scale of $10^n$. As shown, the photon counts range from 1 (representing a de minimus value) and 100,000. The photon counts for the probes in the wild-type cell numbered "45" is around 10,000.

At various wild-type cells, the photon count for the probes in the cells drops to 1 or lower. For example, the photon counts for wild-type cells numbered 11, 24, 39, etc. are 1. The low photon counts are due to the fact that there are no probes in these cells. The cells are left "blank" in order to minimize diffraction edges and thus, the location of these blank cells is known consequently, the intermittent wild-type cells that have a photon count of 1 do not represent erroneous data.

As shown in FIG. 14A, the scaled photon counts for the wild-type probes hybridizing with the sample and reference sequences are almost the same except for two "bubbles." A bubble 730 has a top curve defined by the photon counts of the wild-type probes that hybridized with the reference sequence and a bottom curve defined by the photon counts of the wild-type probes that hybridized with the sample sequence. Following bubble 730, there is a section 732 where the photon counts for the wild-type probes hybridizing with the sample and reference sequences are almost the same. After section 732 is another bubble 734 which again has a top curve defined by the hybridization of the reference sequence and the bottom curve defined by the hybridization of the sample sequence. Another partial bubble is shown to the right of bubble 734.

Each bubble in FIG. 14A corresponds to a dark region surrounding a single mutation. Because the wild-type probes at and surrounding a mutant position in the sample sequence contain a single base mismatch with the sample sequence, the hybridization is relatively lower which results in lower photon counts. Much information about the sample sequence may be acquired by a detailed analysis of these bubble regions.

The width of the bubble indicates whether there is a false positive, a single mutation or a multiple mutation. If there is a single mutation, the width of the bubble should be approximately equal to the probe length. For example, FIG. 14A was produced utilizing 20-mer probes. Accordingly, bubbles 730 and 734 are approximately 20 wild-type cells wide indicating that the both these bubbles were produced by single mutations. The width of the dark region resulting from a single mutation is believed to be approximately equal to the probe length because each of the probes in this region have a single base mismatch with the sample sequence.

If the width of the bubble is substantially less than the probe length, the bubble may represent a false positive. For example, assume that at wild-type cell number 45 in FIG. 14A, the hybridization of the wild-type probe with the sample sequence was very low (e.g., around 1000 photon counts). A base calling algorithm that calls the bases according to the intensities among the cells at that position may indicate that there is a mutation at this position. However, the low photon counts may be due to dust on the chip and not due to lower hybridization. Since the width of this bubble would be 1, which is substantially lower than the probe width of 20, the lower photon count at wild-type cell 45 would not be due to a mutation (i.e., there is no dark region surrounding that position).

If the width of the bubble is substantially more than the probe length, the bubble may represent multiple mutations. In other words, the bubble may be produced by more than one overlapping dark region. The analysis of such a bubble will be discussed in more detail in reference to FIG. 14C.

Returning to FIG. 14A, each of bubbles 730 and 734 are approximately 20 bases wide indicating with a high degree of certainty that each of the bubbles represent a single mutation. Furthermore, the bubbles may be analyzed to determine the probable location of the mutations within the bubbles. As mentioned earlier, the 20-mer probes on the chip had an interrogation position at the $12^{th}$ base position in the probe. Thus, the base at the $12^{th}$ base position is the base that varies among the related WT-, A-, C-, G- and T-cells. Accordingly, the mutation should be located at the $12^{th}$ position in the bubble.

The actual mutation in bubble 730 occurs at the 12th position (from the left). Additonally, the actual mutation in bubble 734 occurs at the 12th position (from the left). Thus, as the graph shows, there are 11 bases to the left of each mutation and 8 bases to the right of each mutation. By utilizing the location of the interrogation position within the probes, the present invention can help to identify the probable location of a mutation within a dark region or bubble.

Additionally, because this method identifies specific locations that may have a mutation, more efficient base calling may be achieved. For example, an analysis of bubble 730 indicates that there is likely to be a single mutation around wild-type cell 15. Typically, most errors in base calling occur in the dark regions surrounding a mutation. Many false positives in this dark zone can now be eliminated because they are incompatible with the bubble size (which indicates single mutation, for example). Also, by identifying clearly a "mismatch zone," we can now apply algorithms that factor in the effect of a mismatch or multiple mismatches.

Figure 14B:
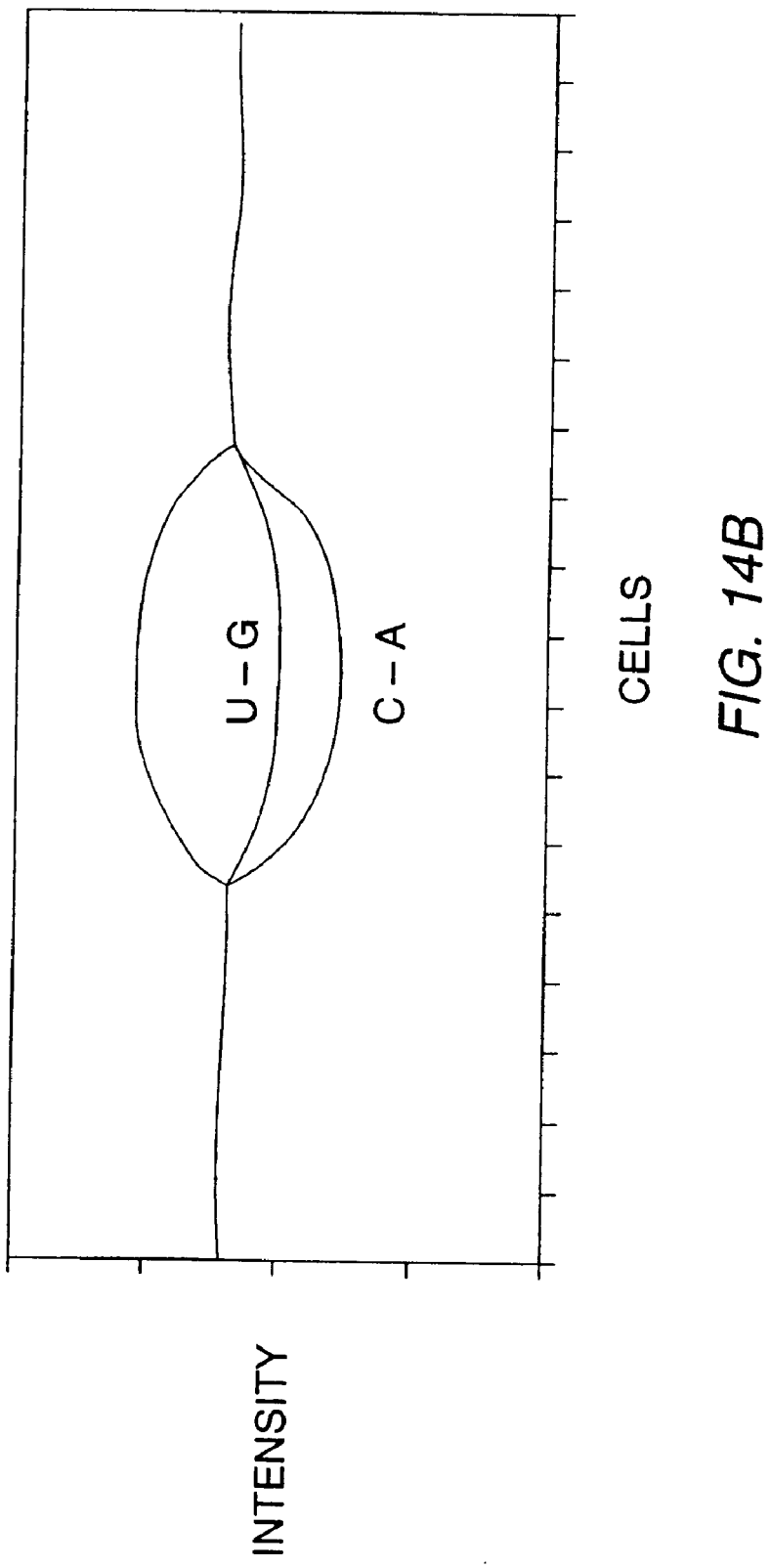

Additionally, the shape of the bubble may indicate what mutation has occurred. FIG. 14B shows a hypothetical graph of the fluorescent intensities vs. cell locations for wild-type probes hybridizing with two sample sequences and one reference sequence. A C-A mismatch will be more destabilizing to probe hybridization than a U-G mismatch. As shown, the more destabilizing C-A mismatch results in a larger volume bubble. The shape of the bubble may be utilized to identify the particular mutation by pattern matching bubbles stored in a library.

Figure 14C:
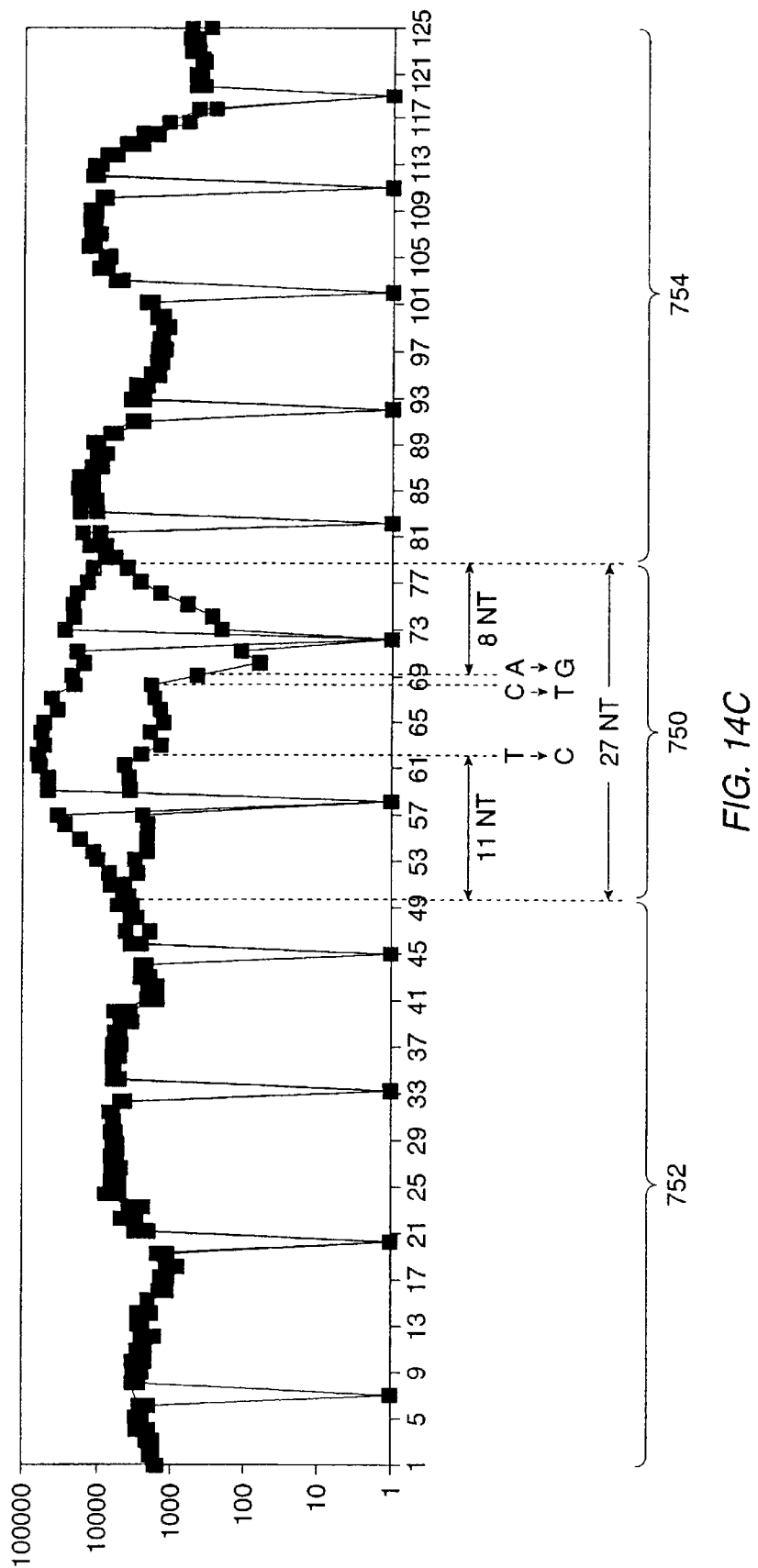

FIG. 14C shows a graph of the fluorescent intensities (photon counts) of the wild-type probes hybridizing with the sample and reference sequences. A single bubble 750 is flanked on either side by regions 752 and 754 which do not contain a mutation. The graph was produced from a chip containing 20-mer probes with an interrogation position at base 12 on the probes.

As shown, bubble 750 is 27 bases wide indicating that the bubble was produced from the dark regions surrounding more than one mutation as 27 is greater than 20 or the length of the probes. In addition to providing information that there are multiple mutations, analysis of the bubble indicates the probable position of two of the mutations. Because the interrogation position is at base 12 in the 20-mer probes, one of the mutations should be around 12 bases from the left end of the bubble while another mutations should be around 8 bases from the right end of the bubble. And in fact, there is a mutation of T to C at wild-type cell 62 which is 12 bases from the left of the bubble. Additionally, there is a mutation of A to G at wild-type cell 69 which is 8 bases from the right of the bubble.

The third and last mutation within bubble 750 may be identified by performing base calling methods within the bubble. Alternatively, the mutation may be identified by pattern matching bubbles from a library that indicate not only the number of mutations but also the specific location and type of mutation.

Figure 15:
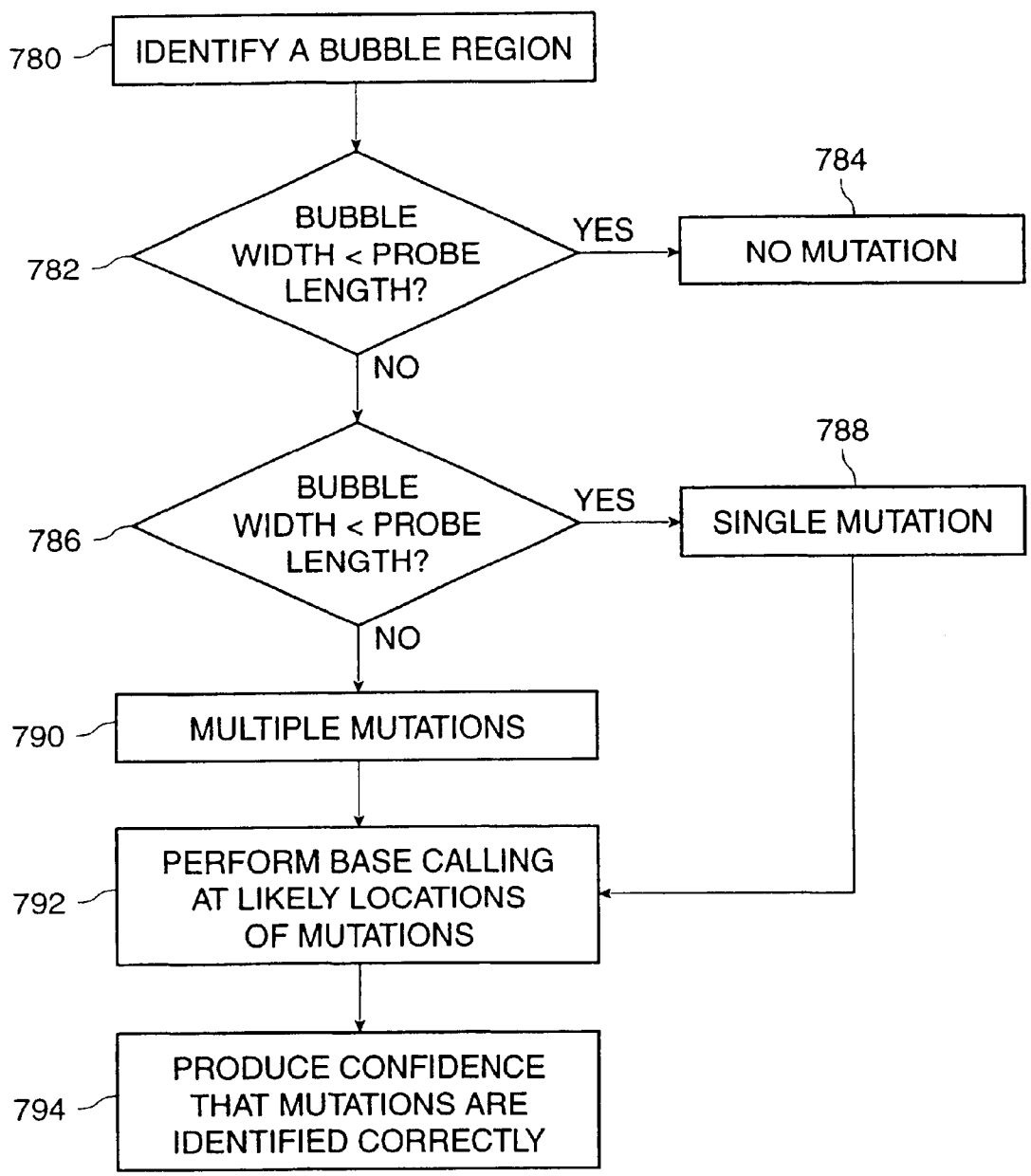
FIG. 15 illustrates the high level flow of an embodiment that uses the hybridization data from than one base position to identify mutations in a sample sequence.

FIG. 15 illustrates the high level flow of one embodiment of the present invention that uses the hybridization data from more than one base position to identify mutations in a sample nucleic acid sequence. After probe intensities from the hybridization of wild-type probes with a sample and reference sequence are measured, the system identifies a bubble region at step 780. Bubble regions are identified as regions where the hybridization of the wild-type probes to the sample and reference sequence differ significantly. Additionally, the reference sequence should hybridize more strongly with the wild-type probes since the wild-type probes will be perfectly complementary to the reference sequence.

At step 782, the system compares the base width of the bubble to the probe length. If the bubble width is substantially less than the probe length, the bubble does not represent a mutation at step 784. The determination of how much less the bubble width may vary according to experiment conditions.

At step 786, the system compares the base width of the bubble to the probe length to determine if they are approximately equal. If the bubble width is approximately equal to the probe length, the bubble represents a single base mutation at step 788. Again, the determination of how close the bubble width should be to the probe length may vary according to experiment conditions.

If the bubble width is substantially more than the probe length, the bubble represents multiple mutations at step 790. The system performs base calling at likely locations of mutations at step 792. The likely locations of mutations are determined by both the width of the bubble and the location of the interrogation position on the probes. Additionally, the system may analyze the pattern of the bubble to determine the specific mutations and their positions by analyzing the pattern of the bubble. The base calling method with the present invention may be the intensity ratio method, reference method, statistical method, or any other method.

At step 794, the system produces confidences that the mutations are identified correctly. Each confidence is determined by how closely the experimental data matched the data expected for the mutation that was called. For example, if the bubble width was exactly the same as the probe length and the base calling method identified a mutation at the interrogation position in the probes, there is a very high likelihood or probability that the mutation was identified correctly. The confidence may also be produced according to how closely the bubble pattern matched the pattern for that mutation or mutations in the library of patterns.

Although in a preferred embodiment, this method of identifying mutations in a sample nucleic acid sequence is utilized in conjunction with pooling processing in order to reduce variations, the method may be utilized without pooling processing. For example, the method may be utilized effectively where the variations between separate experiments is minimized or the data is adjusted accordingly. Therefore, this method is not limited to the embodiment discussed above.

The present invention provides methods of accurately identifying single mutations, locating multiple mutations and removing false positives for mutations. These methods are advantageously performed with pooling processing and utilize hybridization data from more than one base position to identify the likely position of mutations. The interrogation position on the probes is also utilized to more accurately identify the likely position of mutations which makes more efficient use of base calling methods.

VI. Comparative Analysis (ViewSeq™)

The present invention provides a method of comparative analysis and visualization of multiple experiments. The method allows the intensity ratio, reference, and statistical methods to be run on multiple datafiles simultaneously. This permits different experimental conditions, sample preparations, and analysis parameters to be compared in terms of their effects on sequence calling. The method also provides verification and editing functions, which are essential to reading sequences, as well as navigation and analysis tools.

Figure 16:
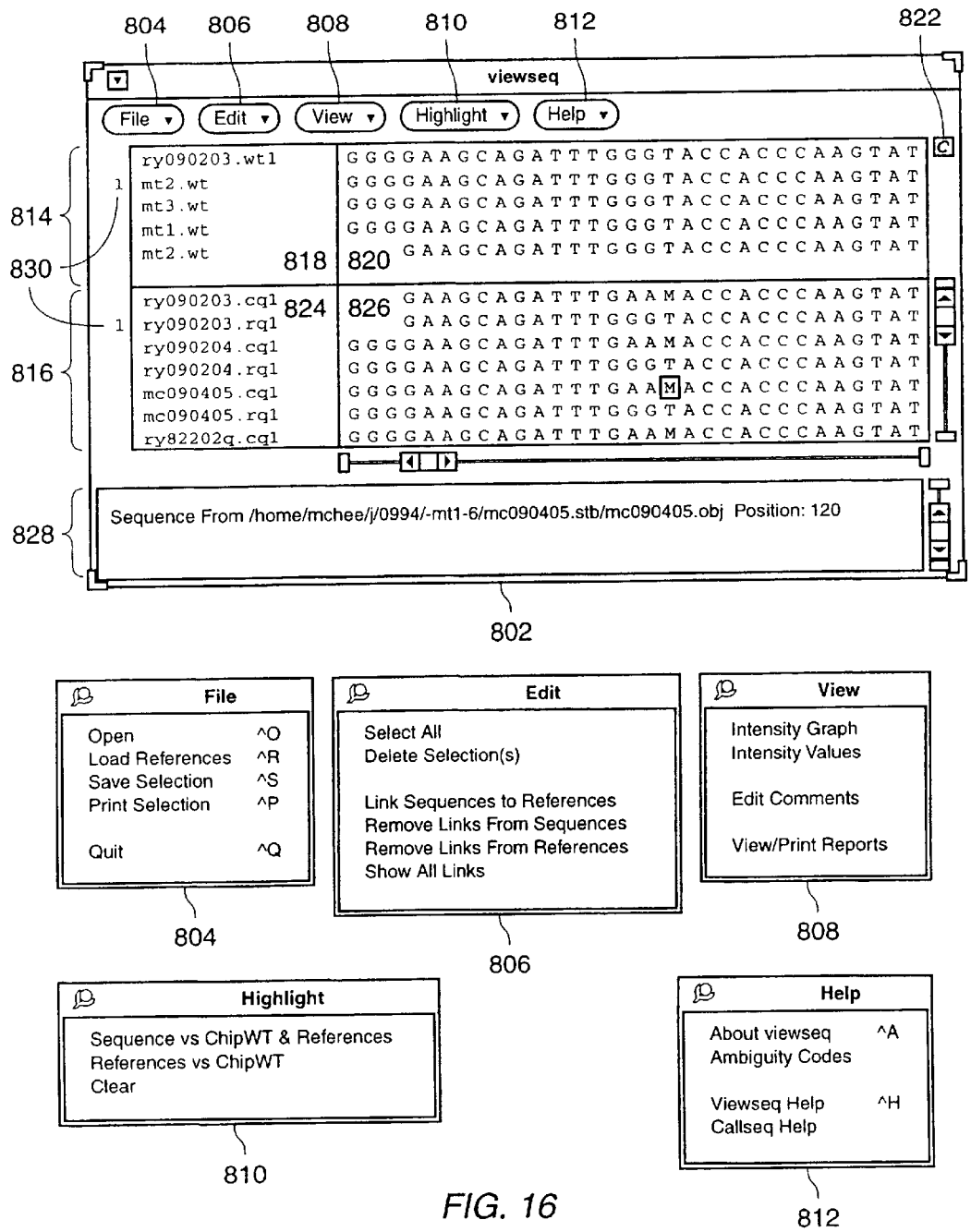
FIG. 16 illustrates the main screen and the associated pull down menus for comparative analysis and visualization of multiple experiments.

FIG. 16 illustrates the main screen and the associated pull down menus for comparative analysis and visualization of multiple experiments (SEQ ID NO:8 and SEQ ID NO:9). The windows shown are from an appropriately programmed Sun Workstation. However, the comparative analysis software may also be implemented on or ported to a personal computer, including IBM PCs and compatibles, or other workstation environments. A window 802 is shown having pull down menus for the following functions: File 804, Edit 806, View 808, Highlight 810, and Help 812.

The main section of the window is divided into a reference sequence area 814 and a sample sequence area 816. The reference sequence area is where known sequences are displayed and is divided into a reference name subarea 818 and reference base subarea 820. The reference name subarea is shown with the filenames that contain the reference sequences. The chip wild-type is identified by the filename with the extension ".wt#" where the # indicates a unit on the chip. The reference base subarea contains the bases of the reference sequences. A capital C 822 is displayed to the right of the reference sequence that is the chip wild-type for the current analysis. Although the chip wild-type sequence has associated fluorescence intensities, the other reference sequences shown below the chip wild-type may be known sequences that have not been tiled on the chip. These may or may not have associated fluorescence intensities. The reference sequences other than the chip wild-type are used for sequence comparisons and may be in the form of simple ASCII text files.

Sample sequence area 816 is where sample or unknown experimental sequences are displayed for comparison with the reference sequences. The sample sequence area is divided into a sample name subarea 824 and sample base subarea 826. The sample name subarea is shown with filenames that contain the sample sequences. The filename extensions indicate the method used to call the sample sequence where ".cq#" denotes the intensity ratio method, ".rq#" denotes the reference method, and ".sq#" denotes the statistical method (# indicates the unit on the chip). The sample base subarea contains the bases of the sample sequences. The bases of the sample sequences are identified by the codes previously set forth which, for the most part, conform to the IUPAC standard.

Window 802 also contains a message panel 828. When the user selects a base with an input device in the reference or sample base subarea, the base becomes highlighted and the pathname of the file containing the base is displayed in the message panel. The base's position in the nucleic acid sequence is also displayed in the message panel.

In pull down menu File 804, the user is able to load files of experimental sequences that have been tiled and scanned on a chip. There is a chip wild-type associated with each experimental sequence. The chip wild-type associated with the first experimental sequence loaded is read and shown as the chip wild-type in reference sequence area 814. The user is also able to load files of known nucleic acid sequences as reference sequences for comparison purposes. As before, these known reference sequences may or may not have associated probe intensity data. Additionally, in this menu the user is able to save sequences that are selected on the screen into a project file that can be loaded in at a later time. The project file also contains any linkage of the sequences, where sequences are linked for comparison purposes. Sequences to be saved, both reference and sample, are chosen by selecting the sequence filename with an input device in the reference or sample name subareas.

In pull down menu Edit 806, the user is able to link together sequences in the reference and sample sequence areas. After the user has selected one reference and one or more sample sequences, the sample sequences can be linked to the reference sequence by selecting an entry in the pull down menu. Once the sequences are linked, a link number 830 is displayed next to each of sequences of related interest. Each group of linked sequences is associated with a unique link number, so the user can easily identify which sequences are linked together. Linking sequences permits the user to more easily compare the linked sequences. The user is also able to remove and display links from this menu.

In pull down menu View 808, the user is able to display intensity graphs for selected bases. Once a base is selected in the reference or sample base subareas, the user may request an intensity graph showing the hybridized probe intensities of the selected base and a delineated neighborhood of bases near the selected base. Intensity graphs may be displayed for one or multiple selected bases. The user is also able to prepare comment files and reports in this menu.

Figure 17:
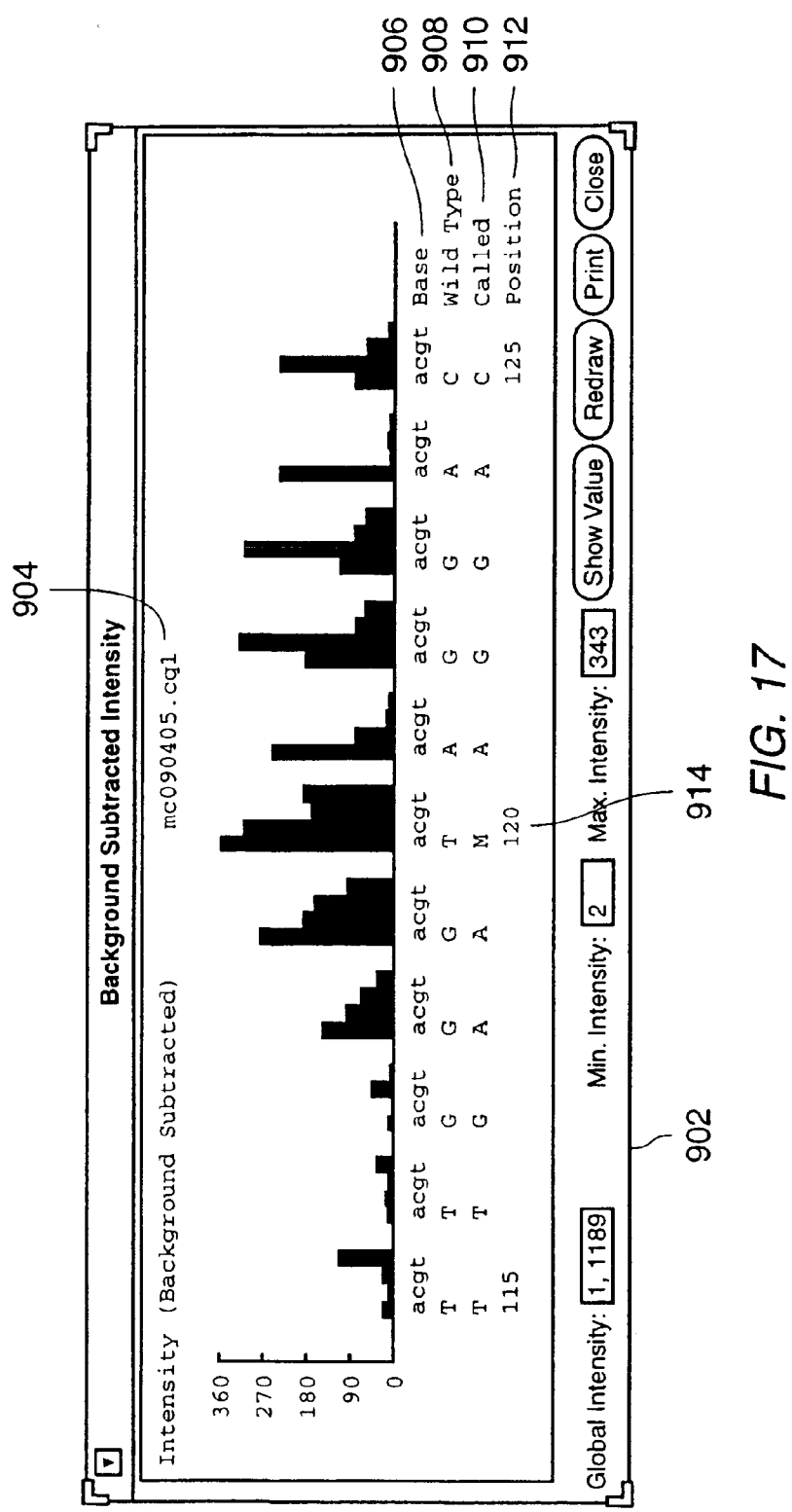
FIG. 17 illustrates an intensity graph window for a selected base.

FIG. 17 illustrates an intensity graph window for a selected base at position 120 (SEQ ID NO:30 and SEQ ID NO:31). The filename containing the sequence data is displayed at 904. The graph shows the intensities for each of the hybridized probes associated with a base. Each grouping of four vertical bars on the graph, which are labeled as "a", "c", "g", and "t" on line 906, shows the background subtracted intensities of probes having the indicated substitution base. In one embodiment, the called bases are shown in red. The wild-type base is shown at line 908, the called base is shown at line 910, and the base position is shown at line 912. In FIG. 17, the base selected is at position 120, as shown by arrow 914. The wild-type base at this position is T; however, the called base is M which means the base is either A or C (amino). The user is able to use intensity graphs to visually compare the intensities of each of the possible calls.

Figure 18:
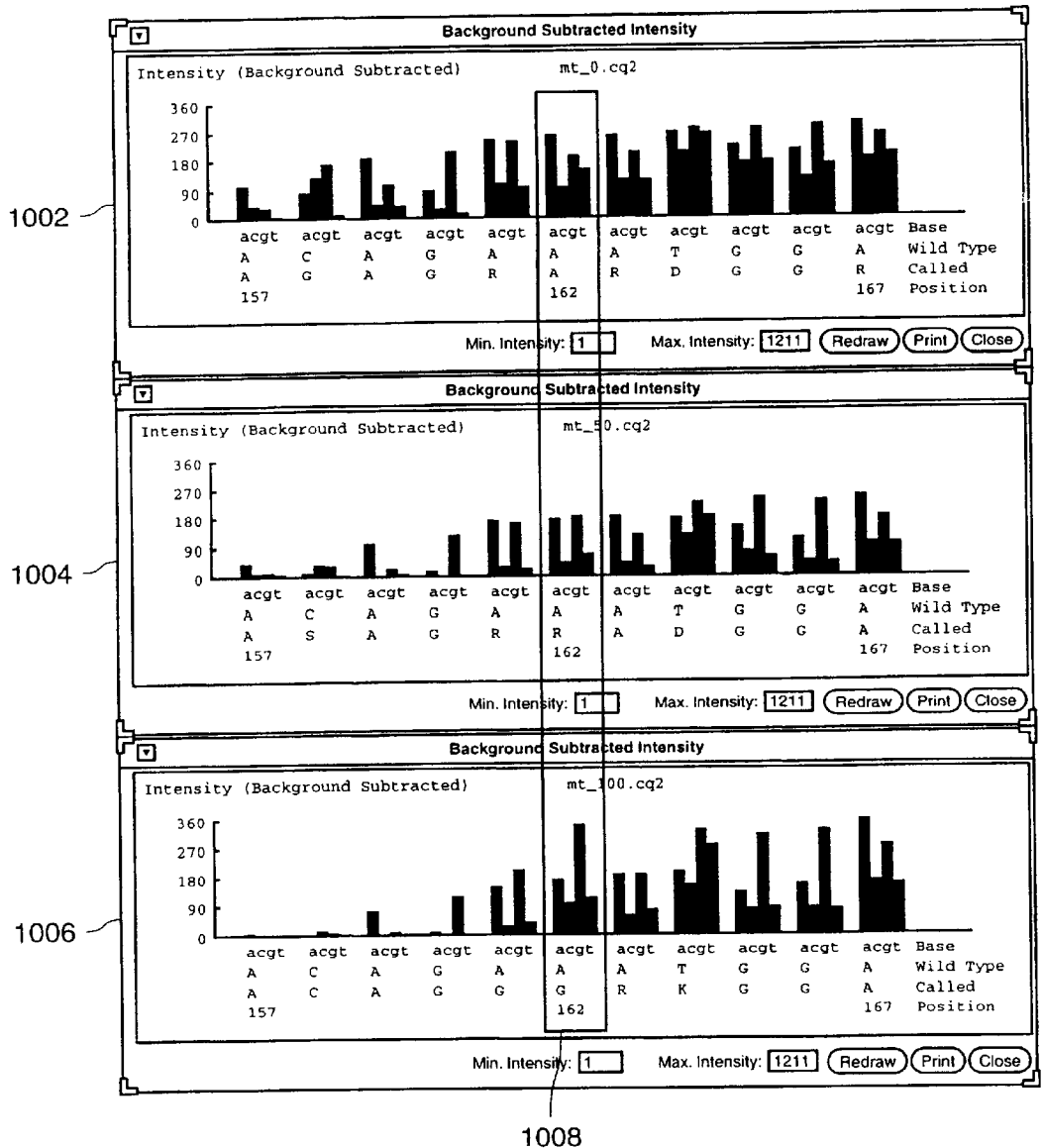
FIG. 18 illustrates multiple intensity graph windows for selected bases.

FIG. 18 illustrates multiple intensity graph windows for selected bases (SEQ ID NO:32, SEQ ID NO:33, SEQ ID NO:34, and SEQ ID NO:35). There are three intensity graph windows 1002, 1004, and 1006 as shown. Each window may be associated with a different experiment, where the sequence analyzed in the experiment may be either a reference (if it has associated probe intensity data as in the chip wild-type) or a sample sequence. The windows are aligned and a rectangular box 1008 shows the selected bases' position in each of the sequences (position 162 in FIG. 18). The rectangular box aids the user in identifying the selected bases.

Referring again to FIG. 16, in pull down menu Highlight 810, the user is able to compare the sequences of references and samples. At least four comparisons are available to the user, including the following: sample sequences to the chip wild-type sequence, sample sequences to any reference sequences, sample sequences to any linked reference sequences, and reference sequences to the chip wild-type sequence. For example, after the user has linked a reference and sample sequence, the user can compare the bases in the linked sequences. Bases in the sample sequence that are different from the reference sequence will then be indicated on the display device to the user (e.g., base is shown in a different color). In another example, the user is able to perform a comparison that will help identify sample sequences. After a sample is linked to multiple reference sequences, each base in the sample sequence that does not match the wild-type sequence is checked to see if it matches one of the linked reference sequences. The bases that match a linked reference sequence will then be indicated on the display device to the user. The user may then more easily identify the sample sequence as being one of the reference sequences.

In pull down menu Help 812, the user is able to get information and instructions regarding the comparative analysis program, the calling methods, and the IUPAC definitions used in the program.

Figure 19:
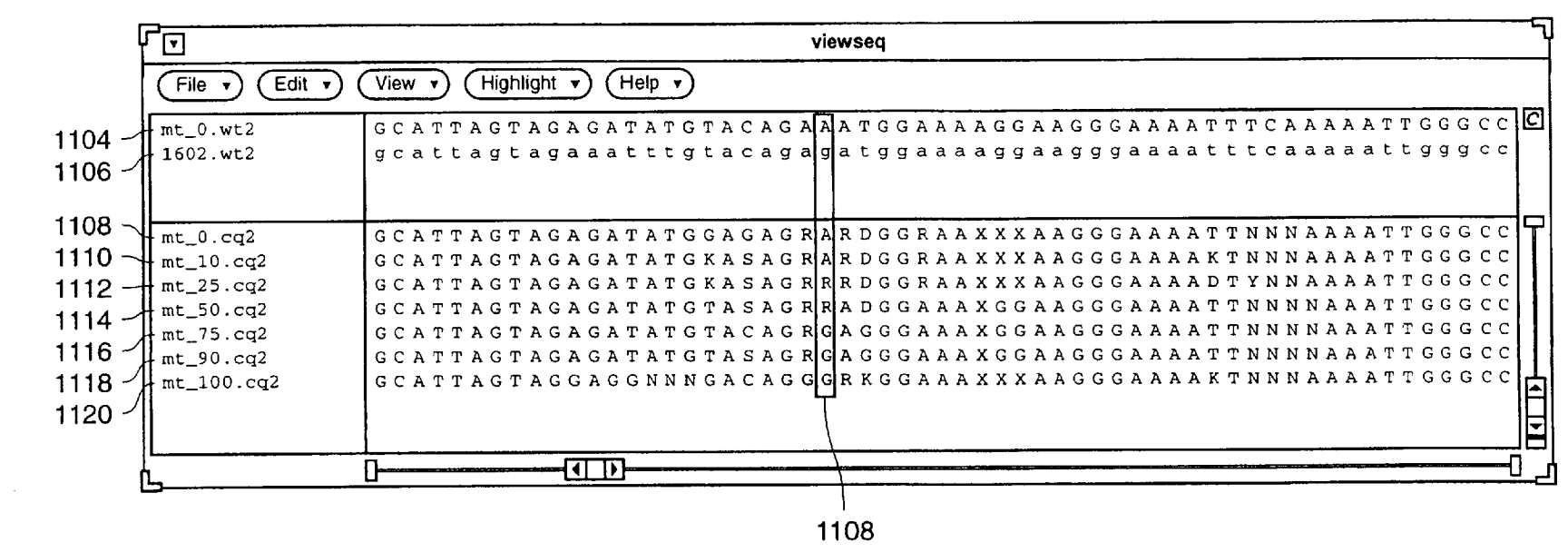

FIG. 19 illustrates the intensity ratio method correctly calling a mutation in solutions with varying concentrations (SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18). A window 1102 is shown with a chip wild-type 1104 and a mutant sequence 1106. The mutant sequence differs from the chip wild-type at the position indicated by the rectangular box 1108. The chip wild-type and mutant sequences are a region of HIV Pol Gene spanning mutations occurring in AZT drug therapy.

There are seven sample sequences that are called using the intensity ratio method. The sample sequences are actually solutions of different proportions of the chip wild-type sequence and the mutant sequence. Thus, there are sample solutions 1110, 1112, 1114, 1116, 1118, 1120, and 1122. The solutions are 15-mer tilings across the chip wild-type with increased percentages of the mutant sequence from 0 to 100% by weight. The following shows the proportions of the sample solutions:

| Sample Solution | Chip Wild-Type:Mutant |
|---|---|
| 1110 | 100:0 |
| 1112 | 90:10 |
| 1114 | 75:25 |
| 1116 | 50:50 |
| 1118 | 25:75 |
| 1120 | 10:90 |
| 1122 | 0:100 |

For example, sample solution 1114 contains 75% chip wild-type sequence and 25% mutant sequence.

Now referring to the bases called in rectangular box 1108 for the sample solutions, the intensity ratio method correctly calls sample solution 1110 as having a base A as in the chip-wild type sequence. This is correct because sample solution 1110 is 100% chip wild-type sequence. The intensity ratio method also calls sample solution 1112 as having a base A because the sample solution is 90% chip wild-type sequence.

The intensity ratio method calls the identified base in sample solutions 1114 and 1116 as being an R, which is an ambiguity IUPAC code denoting A or G (purine). This also a correct base call because the sample solutions have from 75% to 50% chip-wild type sequence and from 25% to 50% mutation sequence. Thus, the intensity ratio method correctly calls the base in this transition state.

Sample solutions 1118, 1120, and 1122 are called by the intensity ratio method as having a mutation base G at the specified location. This is a correct base call because the sample solutions primarily consist of the mutation sequence (75%, 90%, and 100% respectively). Again, the intensity ratio method correctly called the bases.

These experiments also show that the base calling methods of the present invention may also be used for solutions of more than one nucleic acid sequence.

Figure 20:
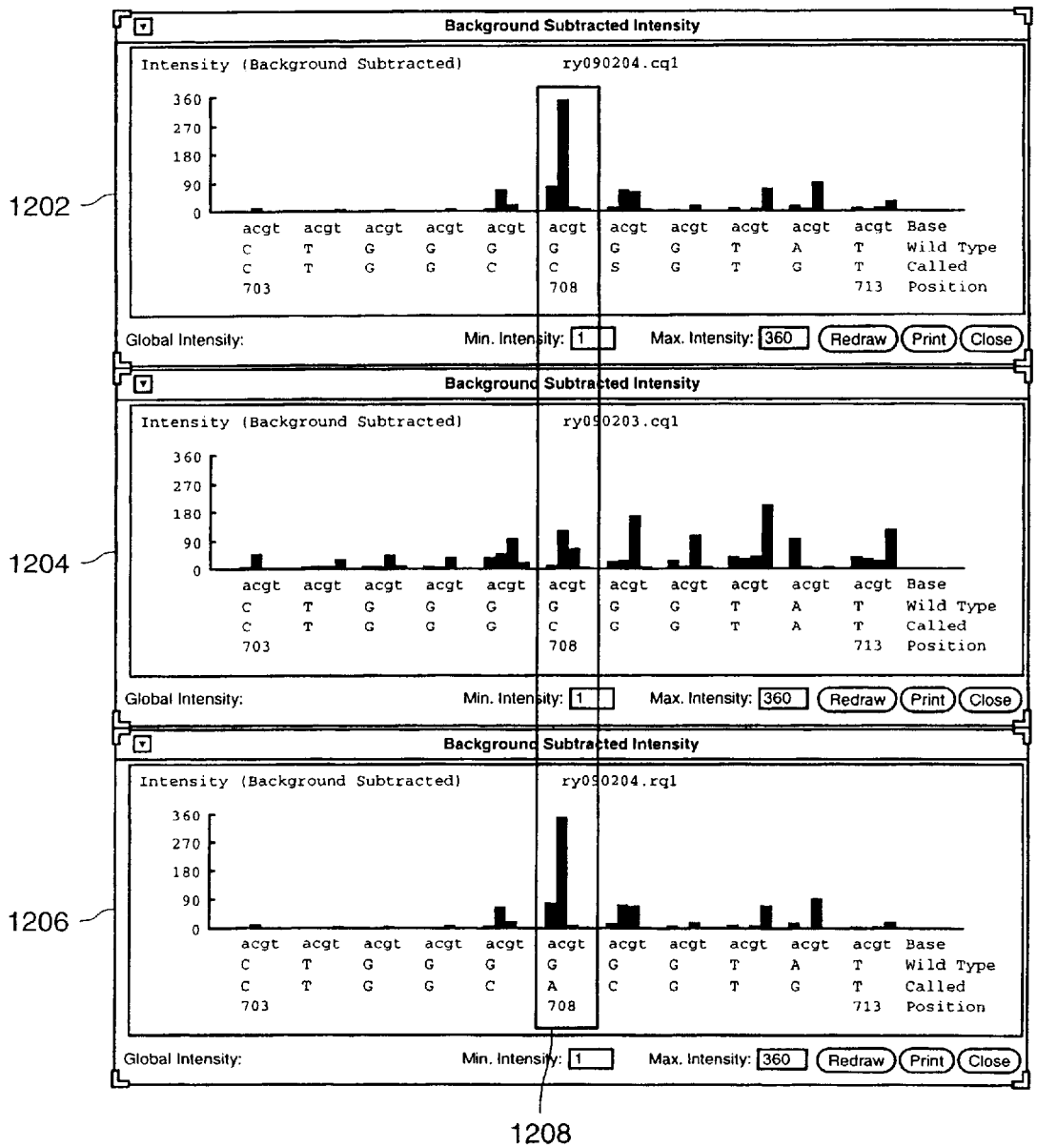
FIG. 20 illustrates the reference method correctly calling a mutant base where the intensity ratio method incorrectly called the mutant base.

FIG. 20 illustrates the reference method correctly calling a mutant base where the intensity ratio method incorrectly called the mutant base (SEQ ID NO:36, SEQ ID NO:37, SEQ ID NO:38, and SEQ ID NO:39). There are three intensity graph windows 1202, 1204, and 1206 as shown. The windows are aligned and a rectangular box 1208 outlines the bases of interest. Window 1202 shows a sample sequence called using the intensity ratio method. However, the base in the rectangular box 1208 was incorrectly called base C, as there is actually a base A at that position. The intensity ratio method incorrectly called the base as C because the probe intensity associated with base C is much higher than the other probe intensities.

Window 1204 shows a reference sequence called using the intensity ratio method. As the reference sequence is known, it is not necessary to know the method used to call the reference sequence. However, it is important to have probe intensities for a reference sequence to use the reference method. The reference sequence is called a base C at the position indicated by the rectangular box.

Window 1206 shows the sample sequence called using the reference method. The reference method correctly calls the specified base as being base A. Thus, for some cases the reference method is preferable to the intensity ratio method because it compares probe intensities of a sample sequence to probe intensities of a reference sequence.

VII. EXAMPLES

EXAMPLE 1

The intensity ratio method was used in sequence analysis of various polymorphic HIV-1 clones using a protease chip. Single stranded DNA of a 382 nt region was used with 4 different clones (HXB2, SF2, NY5, pPol4mut18). Results were compared to results from an ABI sequencer. The results are illustrated below:

|  | ABI | | Protease Chip | |
|---|---|---|---|---|
|  | Sense | Antisense | Sense | Antisense |
| No call | 0 | 4 | 9 | 4 |
| Ambiguous | 6 | 14 | 17 | 8 |
| Wrong call | 2 | 3 | 3 | 1 |
| TOTAL | 8 | 21 | 29 | 13 |
| SUMMARY | | | | |
| ABI (sense) - 99.5% | | | | |
| Chip (sense) - 98.1% | | | | |
| ABI (antisense) - 98.6% | | | | |
| Chip (antisense) - 99.1% | | | | |

EXAMPLE 2

HIV protease genotyping was performed using the described chips and CallSeq™ intensity ratio calculations. Samples were evaluated from AIDS patients before and after ddI treatment. Results were confirmed with ABI sequencing.

FIG. 21 illustrates the output of the ViewSeq™ program with four pretreatment samples and four posttreatment samples (SEQ ID NO:22, SEQ ID NO:23, SEQ ID NO:24, SEQ ID NO:25, SEQ ID NO:26, and SEQ ID NO:27). Note the base change at position 207 where a mutation has arisen.

Even adjacent two additional mutations (gt), the "a" mutation has been properly detected.

VIII. Appendices

The Microfiche appendices (copyright Affymetrix, Inc.) provide C++ source code and header files for implementing the present invention. Appendix A contains the source code files (.cc files) for CallSeq™, which is a base calling program that implements the intensity ratio, reference, and statistical methods of the present invention. Appendix B contains the header files (.h files) for CallSeq™. Appendices C and D contain the source code and header files, respectively, for a program that performs a preprocessing stage for the statistical method of CallSeq™.

Appendix E contains the source code and header files for ViewSeq™, which is a comparative analysis and visualization program according to the present invention. Appendices A-E are written for a Sun Workstation.

The above description is illustrative and not restrictive. Many variations of the invention will become apparent to those of skill in the art upon review of this disclosure. Merely by way of example, while the invention is illustrated with particular reference to the evaluation of DNA (natural or unnatural), the methods can be used in the analysis from chips with other materials synthesized thereon, such as RNA. The scope of the invention should, therefore, be determined not with reference to the above description, but instead should be determined with reference to the appended claims along with their full scope of equivalents.

What is claimed is:

1. A method of identifying an unknown base in a sample nucleic acid sequence, comprising:

inputting probe intensities for a plurality of nucleic acid probes that differ by a base at an interrogation position corresponding to the unknown base, each probe intensity indicating hybridization affinity between a nucleic acid probe and the sample nucleic acid sequence;

analyzing the probe intensities and at least one probe intensity from a nucleic acid probe with an interrogation position corresponding to a position near the unknown base in the sample nucleic acid sequence; and generating a base call identifying the unknown base according to results of analyzing the probe intensities and the at least one probe intensity.

2. The method of claim 1, wherein if the at least one probe intensity is not lower as is expected for a mutation, the base call identifies the unknown base as a nonmutant base.

3. The method of claim 1, wherein if the at least one probe intensity is lower as is expected for a mutation, the base call identifies the unknown base as a mutant base.

4. The method of claim 3, wherein the mutant is identified by the one of the plurality of nucleic acid probes with the highest probe intensity.

5. The method of claim 1, wherein the position near the unknown base in the sample nucleic acid sequence is adjacent to the unknown base.

6. The method of claim 1, wherein the interrogation position is at an internal position of the nucleic acid probes.

7. A computer program product that identifies an unknown base in a sample nucleic acid sequence, comprising:

computer code that receives probe intensities for a plurality of nucleic acid probes that differ by a base at an interrogation position corresponding to the unknown base, each probe intensity indicating hybridization affinity between a nucleic acid probe and the sample nucleic acid sequence;

computer code that analyzes the probe intensities and at least one probe intensity from a nucleic acid probe with an interrogation position corresponding to a position near the unknown base in the sample nucleic acid sequence;

computer code that generates a base call identifying the unknown base according to results of analyzing the probe intensities and the at least one probe intensity; and a computer readable medium that stores the computer codes.

8. The computer program product of claim 7, wherein the computer readable medium is a memory, hard drive, floppy disk, CD-ROM, flash memory, or tape.

9. The computer program product of claim 7, wherein if the at least one probe intensity is not lower as is expected for a mutation, the base call identifies the unknown base as a nonmutant base.

10. The computer program product of claim 7, wherein if the at least one probe intensity is lower as is expected for a mutation, the base call identifies the unknown base as a mutant base.

11. The computer program product of claim 10, wherein the mutant is identified by the one of the plurality of nucleic acid probes with the highest probe intensity.

12. The computer program product of claim 7, wherein the position near the unknown base in the sample nucleic acid sequence is adjacent to the unknown base.

13. The computer program product of claim 7, wherein the interrogation position is at an internal position of the nucleic acid probes.

* * * * *